(12) United States Patent
Durran et al.

(10) Patent No.: US 11,857,625 B2
(45) Date of Patent: Jan. 2, 2024

(54) PHARMACEUTICAL COMPOSITIONS

(71) Applicant: UCB BIOPHARMA SRL, Brussels (BE)

(72) Inventors: Sandrine Durran, Slough (GB); Andrew Jeffrey Yates, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 664 days.

(21) Appl. No.: 16/765,786

(22) PCT Filed: Nov. 13, 2018

(86) PCT No.: PCT/EP2018/081129
§ 371 (c)(1),
(2) Date: May 20, 2020

(87) PCT Pub. No.: WO2019/101582
PCT Pub. Date: May 31, 2019

(65) Prior Publication Data
US 2021/0106683 A1    Apr. 15, 2021

(30) Foreign Application Priority Data
Nov. 23, 2017 (GB) ..................... 1719447

(51) Int. Cl.
A61K 39/395    (2006.01)
A61K 47/12     (2006.01)
A61K 47/18     (2017.01)
A61K 47/26     (2006.01)
C07K 16/24     (2006.01)

(52) U.S. Cl.
CPC ........ A61K 39/39591 (2013.01); A61K 47/12 (2013.01); A61K 47/183 (2013.01); A61K 47/26 (2013.01); C07K 16/244 (2013.01); C07K 2317/76 (2013.01)

(58) Field of Classification Search
None
See application file for complete search history.

(56) References Cited

U.S. PATENT DOCUMENTS

| 8,580,265 B2 * | 11/2013 | Adams .................. A61P 19/00 |
| | | 530/387.3 |
| 2013/0121991 A1 | 5/2013 | Huille et al. |
| 2013/0216525 A1 | 8/2013 | Chen |
| 2015/0150979 A1 * | 6/2015 | Yates ................. C07K 16/2803 |
| | | 424/133.1 |
| 2019/0256588 A1 | 8/2019 | Song et al. |

FOREIGN PATENT DOCUMENTS

| MX | 2012007676 A | 8/2012 |
| WO | 2007/019232 A3 | 2/2007 |
| WO | 2009/120684 A1 | 10/2009 |
| WO | WO-2011/088120 A1 | 7/2011 |
| WO | WO-2011080209 A2 | 7/2011 |
| WO | 2012/095662 A1 | 7/2012 |
| WO | 2016/103153 A1 | 6/2016 |
| WO | 2017/031288 A1 | 2/2017 |
| WO | 2017/072183 A1 | 5/2017 |
| WO | 2017/180594 A1 | 10/2017 |

OTHER PUBLICATIONS

Bajaj et al., "Determination of Second Virial Coefficient of Proteins Using a Dual-Detector Cell for Simultaneous Measurement of Scattered Light Intensity and Concentration in SEC-HPLC," Biophys. J. 87(6): 4048-4055 (2004).
Daugherty et al., "Formulation and Delivery Issues for Monoclonal Antibody Therapeutics," Advanced Drug Delivery Reviews 58: 686-706 (2006).
Search Report issued in GB Application No. GB1719447.3 dated Aug. 15, 2018.

* cited by examiner

*Primary Examiner* — Yunsoo Kim
(74) *Attorney, Agent, or Firm* — MARSHALL, GERSTEIN & BORUN LLP

(57) ABSTRACT

The present invention relates to pharmaceutical compositions comprising from an antibody or a fragment thereof which binds IL-17A and IL-17F and a combination of glycine, acetate buffer at pH 4.6 to 5.5 and polysorbate 80.

9 Claims, No Drawings

Specification includes a Sequence Listing.

PHARMACEUTICAL COMPOSITIONS

REFERENCE TO AN ELECTRONIC SEQUENCE LISTING

The content of the electronic sequence listing (0089-0030US1_SL2.txt; Size: 12.0 KB; and Date of Creation Aug. 6, 2020) is herein incorporated by reference in its entirety.

FIELD OF THE INVENTION

The present invention belongs to the field of pharmaceutical formulations. More specifically, it relates to a pharmaceutical composition comprising an antibody, glycine, acetate buffer and polysorbate 80.

BACKGROUND OF THE INVENTION

The number of biologics gaining approval since the early days of recombinant DNA technologies has climbed and whilst the field remained dynamic in terms of types of biologics, indications targeted and mechanistic basis of drug activity, in recent years, the approval of antibodies-based therapies have by far outnumbered the approval of other biologics.

In order for an antibody therapy to be administered in a patient-friendly manner, mode and time of administration are critical. These aspects are especially important in chronic diseases where patients rely on the drug to carry out living a life as close as possible as that lived by healthy individuals. Drugs requiring long time of administration possibly with hospitalization are generally not seen as patient-friendly. Subcutaneous administration performed in the comfort setting of a patient's home is highly sought. However, a whole plethora of problems arise when antibodies need to be formulated at high concentrations in liquid formulations such as those which are administered subcutaneously and directly by a patient.

Antibodies, whilst being fairly stable molecules, when stored over a period of time, may suffer from chemical and physical instability. Typical chemical instability may result in deamidation, hydrolysis, oxidation, beta-elimination, disulfide exchange or reduction. Physical instability can result in denaturation, aggregation or precipitation. Both chemical and physical instability are far more pronounced when the antibodies are stored in liquid solution at high concentration. However, liquid highly concentrated antibody water-based formulations are particularly complex; water acts as a reactant or facilitates the transfer of reactants leading to chemical degradation and protein instability. There is no simple, universal protocol in formulating antibodies at high concentrations and whilst stabilizers may assist in reducing instability and aggregation, their presence at high concentrations may affect other physico-chemical properties of the final pharmaceutical formulation e.g. viscosity and osmolality.

Avoiding or minimizing aggregation, precipitation or degradation remains a particular challenge. Aggregation, with the formation of soluble matter and/or insoluble precipitate, is a particular problem. This may cause various problems such as aggregates' formation which could lead to immunological reactions upon administration and/or difficulty in performing proper administration of the pharmaceutical formulation, e.g. by causing blockage of the delivery device.

Problems may also arise during the preparation of the antibody at high concentration and the processability of the formulation, seen as how well the formulation behaves through the various manufacturing steps, including filtration, appearance of turbidity and long-term stability, is a very important aspect of pharmaceutical formulation manufacturing and a further hurdle to overcome.

Studies performed at low antibody concentration often do not translate well when the antibody is formulated at high concentration. Depending on the nature of the antibody and the necessary excipients, high scale production may be unexpectedly affected.

Unquestionably, a successful pharmaceutical formulation is achieved by identifying the best combination of all these factors.

Given the above, there remains a need in the art to provide further improved pharmaceutical compositions of therapeutic antibodies.

SUMMARY OF THE INVENTION

The present invention addresses the above-identified need by providing pharmaceutical compositions comprising an antibody; or an antigen-binding fragment thereof, with suitable physico-chemical properties.

The following specific embodiments are described as numbered hereinafter:

Embodiment 1: A pharmaceutical composition comprising:
 a. from about 80 mg/ml to about 200 mg/ml of an antibody, or an antigen-binding fragment thereof, having a heavy chain variable region comprising SEQ ID NO:1 and a light chain variable region comprising SEQ ID NO:2;
 b. acetate;
 c. glycine;
 d. polysorbate 80 and;
 having pH of from about 4.6 to about 5.5 or from about 4.6 to about 5.3.

Embodiment 2: The pharmaceutical composition according to embodiment 1, comprising from about 120 mg/ml to about 185 mg/ml of the antibody, or antigen-binding fragment thereof, preferably about 160 mg/mL.

Embodiment 3: The pharmaceutical composition according to embodiment 1 or embodiment 2, wherein the composition comprises from about 0.01% to about 0.07% (w/v) polysorbate 80.

Embodiment 4: The pharmaceutical composition according to any one of the preceding embodiments, wherein the composition comprises from about 140 mM to about 350 mM of glycine.

Embodiment 5: The pharmaceutical composition according to any one of the preceding embodiments, wherein the composition comprises from about 20 mM to about 100 mM acetate, and preferably from about 40 mM to about 90 mM acetate or from about 50 mM to about 90 mM acetate.

Embodiment 6: The pharmaceutical composition according to any one of the preceding embodiments, wherein the antibody or antigen-binding fragment thereof specifically binds human IL-17A and human IL17F.

Embodiment 7: The pharmaceutical composition according to any one of the preceding embodiments, wherein the composition comprises:
 a. from about 120 mg/mL to about 185 mg/mL of antibody, or antigen-binding fragment thereof;
 b. from about 20 mM to about 100 mM acetate, preferably from about 40 mM to about 90 mM acetate or from about 50 mM to about 90 mM acetate;
 c. from about 140 mM to about 350 mM glycine;
 d. from about 0.01% to about 0.07% (w/v) polysorbate 80,
 wherein the composition has a pH of from about 4.6 to about 5.5 or from about 4.6 to about 5.3.

Embodiment 8: A method for preparing a pharmaceutical composition, wherein the method comprises the steps of:
a. preparing a low concentration formulation by combining from about 40 mg/ml to about 50 mg/ml of an antibody, or an antigen-binding fragment thereof, having a heavy chain variable region comprising SEQ ID NO:1 and a light chain variable region comprising SEQ ID NO:2 with a buffer solution comprising glycine and acetate at pH of from about 4.6 to about 5.5 or from about 4.6 to about 5.3;
b. preparing a high concentration formulation by concentrating the antibody or antigen-binding fragment thereof of the low concentration formulation obtained in a) to a concentration of about 120 mg/ml to about 185 mg/ml;
c. adding polysorbate 80 to the high concentration formulation obtained in b);
d. optionally, before step c) adjusting the concentration of the antibody or antigen-binding fragment thereof with the buffer solution comprising glycine and acetate from about 4.6 to about 5.5 or from about 4.6 to about 5.3.

Embodiment 9: The method according to Embodiment 8, wherein the buffer solution comprises from about 20 mM to about 100 mM acetate, preferably from about 40 mM to about 90 mM acetate or from about 50 mM to about 90 mM acetate and from about 140 mM to about 350 mM glycine and wherein polysorbate 80 is added in step c) to give a final concentration of about 0.01 to about 0.07% (w/v).

Embodiment 10: A pharmaceutical composition obtained by embodiment 8 or embodiment 9.

Embodiment 11: The pharmaceutical composition according to embodiment 10 wherein the pH of the composition is from about 4.6 to about 5.5 or from about 4.6 to about 5.3

Embodiment 12: A container comprising the pharmaceutical composition according to any one of embodiments 1 to 7, 10 or 11.

Embodiment 13: The pharmaceutical composition according to any one of embodiments 1 to 7, 10 or 11 for use in therapy.

Embodiment 14: The pharmaceutical composition according to any one of embodiments 1 to 7, 10 or 11 for use in the treatment or prophylaxis of a pathological disorder mediated by IL-17A and/or IL-17F, or that is associated with increased levels of IL-17A and/or IL-17F.

Embodiment 15: Use of a pharmaceutical composition according to any one of embodiment 1 to 7, 10 or 11 in the manufacture of a medicament for the treatment or prophylaxis of a pathological disorder mediated by IL-17A and/or IL-17F, or that is associated with increased levels of IL-17A and/or IL-17F.

Embodiment 16: A method for treating or preventing a pathological disorder mediated by IL-17A and/or IL-17F, or that is associated with increased levels of IL-17A and/or IL-17F in a mammalian subject comprising administering pharmaceutical composition according to any one of embodiment 1 to 7, 10 or 11.

Embodiment 17: The pharmaceutical composition for use according to embodiment 14, the use according to embodiment 15 or the method according to embodiment 16, wherein the pathological disorder is selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, Crohn's disease, ulcerative colitis, ankylosing spondylitis, axial spondyloarthritis and other spondyloarthropathies.

Embodiment 18: The pharmaceutical composition for use according to embodiment 14, the use according to embodiment 15 or the method according to embodiment 16, wherein the pathological disorder is selected from the group consisting of rheumatoid arthritis, Crohn's disease, ulcerative colitis, psoriasis; psoriatic arthritis; ankylosing spondylitis and axial spondyloarthritis.

DETAILED DESCRIPTION OF THE INVENTION

The invention is based on the combination of polysorbate 80 and a buffer solution comprising an acetate buffer (as a buffering agent) and glycine (as a zwitterion) at pH of from about 4.6 to about 5.5 for preparing a suitable pharmaceutical composition for human use of an antibody, or an antigen binding fragment thereof, having a heavy chain variable region comprising SEQ ID NO:1 and a light chain variable region comprising SEQ ID NO:2, at concentration of from 80 mg/ml to 200 mg/ml, without affecting the processability of the pharmaceutical composition and the long-term stability of the antibody. It is a finding from the inventors that the pharmaceutical compositions according to the invention are stable over time, in particular when stored at 2-25° C., as shown for example at 2-8° C. and 25° C.

The term "stable formulation" refers to a formulation in which the protein of interest (here an antibody or an antigen binding fragment thereof) essentially retains its physical, chemical and/or biological properties upon storage. In order to measure the protein stability in a formulation, various analytical methods are well within the knowledge of the skilled person (see some examples in the example section). Stability is typically assessed at a selected temperature (for instance −70° C., 2-8° C., 25° C., 35° C. or more) for a selected time period (e.g. 3 months, 6 months, 12 months or more). As an antibody; once formulated, is typically stored in the fridge (typically 2-8° C.) or at room temperature (typically 15-25° C.) before being administered to a patient, it is important that said formulated antibody is stable over time at least at 2-25° C., as shown for example at 2-8° C. and 25° C. Various values can be used to conclude about stability over a given time period (in comparison of the initial data), such as (and not limited to): 1) no more than 10% of alteration of the monomeric form of the antibody, 2) no more than 5% of increase in High Molecular Weight Species (HMW or HMWS; also herein referred to as aggregates), 3) no more than 10% of increase in Low Molecular Weight species (LMW or LMWS), or 4) no more than +1-0.3 unit variation of the pH.

In all the embodiments of the invention, "pharmaceutical composition" can also be referred to as "stable pharmaceutical composition" without any differentiation.

In one embodiment of the invention, the pharmaceutical composition according to the invention preferably comprises from or from about 80 mg/ml to or to about 200 mg/mL, preferably from or from about 120 mg/ml to or to about 185 mg/ml or from or from about 120 mg/ml to or to about 180 mg/mL of the antibody; or antigen-binding fragment thereof, such as about 120, 125, 130, 135, 140, 145, 150, 155, 160, 165, 170, 175 or 180 mg/ml, even preferably about 160 mg/mL of the antibody, or antigen-binding fragment thereof.

In another embodiment, the pharmaceutical composition according to the invention composition comprises from or from about 0.01% to or to about 0.07% (w/v) polysorbate 80, such as about 0.01, 0.02, 0.03, 0.04, 0.05, 0.06 or 0.07% (w/v polysorbate 80).

In another embodiment, the pharmaceutical composition according to the invention comprises from or from about 140 mM to or to about 350 mM of glycine. Preferably, the pharmaceutical composition according to the invention comprises from or from about 160 mM to or to about 300 mM of glycine, such as about 160, 170, 180, 190, 200, 210, 220, 230, 240, 250, 260, 270, 280, 290 or 300 mM of glycine. Glycine, in the context of the present invention as a whole, is not a buffering agent. Indeed, at pHs of from about 4.6 to about 5.5, Glycine is a zwitterion. As a zwitterion, it has the ability to interact with hydrophobic and hydrophilic parts of the antibody or antigen-binding fragment thereof therefore possibly reducing self-interaction between the antibody or antigen-binding fragment thereof, providing a stabilizing effect.

In yet another embodiment, the pharmaceutical composition according to the invention as a whole comprises from about 20 mM to about 100 mM acetate, and preferably from about 40 mM to about 90 mM acetate, such as about 40, 45, 50, 55, 60, 65, 70, 75, 80, 85 or 90 mM acetate. Alternatively, the pharmaceutical composition according to the invention as a whole comprises from about 50 mM to about 90 mM acetate, such as about 50, 55, 60, 65, 70, 75, 80, 85 or 90 mM acetate. In one embodiment, the pharmaceutical composition comprises about 55 mM acetate. Acetate, in the context of the present invention as a whole, is the buffering agent. Any kind of acetates can be used such as calcium acetate, magnesium acetate, sodium acetate or zinc acetate. Preferably, sodium acetate is used.

Preferably, the pharmaceutical composition according to the invention does not comprise any sugar (such as monosaccharides, disaccharides or polysaccharides) nor polyol.

The antibody or antigen-binding fragment thereof comprised in the pharmaceutical composition according to the invention specifically binds to human IL-17A and IL-17F.

The term "specifically binds to human IL-17A and IL-17F", "specifically binding to human IL-17A and IL-17F", and equivalents as used herein means the antibody will bind to human IL-17A and IL-17F with sufficient affinity and specificity to achieve a biologically meaningful effect. The antibody selected will normally have a binding affinity for human IL-17A and IL-17F, for example, the antibody may bind human IL-17A and IL-17F with a Kd value of between 100 nM and 1 pM. Antibody affinities may be determined for example by a surface plasmon resonance bases assay, such as the BIAcore assay; enzyme-linked immunoabsorbent assay (ELISA); and competition assays (e.g. RIA's). Within the meaning of the present invention an antibody or antigen-binding fragment thereof specifically binding to human IL-17A and IL-17F may also bind to another molecule, e.g. cyno IL-17A and IL-17F or such as by way of a non-limiting example, in the case where the antibody or antigen-binding fragment thereof is incorporated into a bi- or multi-specific antibody. In particular, the present antibody or antigen-binding fragment thereof does not bind any other human IL-17 isoform other than IL-17A, IL-17F and the IL-17A and IL-17F heterodimer.

IL-17A (originally named CTLA-8) is a pro-inflammatory cytokine and the first IL-17 of the IL-17 family to have been discovered. Subsequently, 5 additional members of the family have been identified (IL-17B to F). IL-17A and F have approximately 55% amino acid sequence homology, they express as homodimers and as heterodimers, signal through the receptors IL-17R, IL-17RC or IL-17RA/RC and have been associated with a number of autoimmune diseases.

The antibody or antigen-binding fragment thereof binding specifically to human IL-17A and IL-17F, preferably also neutralizes human IL-17A and IL-17F.

The term "neutralizes" as used herein refers to an antibody that inhibits or substantially reduces the biological effect of the molecule to which it specifically binds. Therefore, the expression "the antibody neutralizes human IL-17A and IL-17F" refers to an antibody that specifically binds to human IL-17A and IL-17F and inhibits or substantially reduces the biological effect thereof such as by blocking IL-17A and IL-17F binding to their receptor.

The term "antibody" or "antibodies" as used herein refers to monoclonal or polyclonal antibodies and is not limited to recombinant antibodies that are generated by recombinant technologies as known in the art.

The antibody, or antigen-binding fragment thereof, having a variable heavy chain comprising SEQ ID NO:1 and a variable light chain comprising SEQ ID NO:2, as shown in Table 1, is described in more detail in WO2012095662, which content is incorporated herein by reference.

The term "antibody" or "antibodies" also refers to humanized antibodies. Humanized antibodies are antibodies that contain a sequence derived from non-human antibodies. For the most part, humanized antibodies are human antibodies (recipient antibody) in which residues from a hypervariable region of the recipient are replaced by residues from a hypervariable region or complementarity determining region (CDR) of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human diseases. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germline mutant mice results in complete inhibition of endogenous antibody production. Transfer of the human germline immunoglobulin gene array in such germline mutant mice will result in the production of human antibodies with specificity against a particular antigen upon immunization of the transgenic animal carrying the human germline immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. The term "antibody" or "antibodies" as used herein, also refers to an aglycosylated antibody.

The term "antigen-binding fragment thereof" or its grammatical variations as used herein refers to an antibody fragment. Examples of antibody fragments according to the invention include Fab, Fab', F(ab')$_2$, and Fv, scFv fragments, single-chain antibodies, bispecific, trispecific, tetraspecific or multispecific antibodies formed from antibody fragments or antibodies, including but not limited to Fab-Fv or Fab-Fv-Fv constructs. Antibody fragments as defined above are known in the art.

Preferably, the pharmaceutical composition according to the invention comprises (Table 1):
 1) an antibody which comprises a heavy chain having the sequence as defined in SEQ ID NO: 1 and a light chain having the sequence as defined in SEQ ID NO:2
 2) an antibody which comprises a heavy chain having the sequence as defined in SEQ ID NO: 3 and a light chain having the sequence as defined in SEQ ID NO: 4; or
 3) an antibody which comprises a heavy chain having at least 80% identity or similarity, preferably 90% identity or similarity to the variable region of the sequence as defined in SEQ ID NO: 3 and a light chain having at least 80% identity or similarity, preferably 90% identity or similarity to the variable region of the sequence as defined in SEQ ID NO: 4.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

An antibody or an antigen-binding fragment thereof that can be manufactured according to industrial scales can be produced by culturing eukaryotic host cells transfected with one or more expression vectors encoding the recombinant antibody fragment. The eukaryotic host cells are preferably mammalian cells, more preferably Chinese Hamster Ovary (CHO) cells. Mammalian cells may be cultured in any medium that will support their growth and expression of the recombinant protein, preferably the medium is a chemically defined medium that is free of animal-derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large-scale bioreactors are available with a capacity of more than 1,000 L to 50,000 L, preferably between 5,000 L and 20,000 L, or

TABLE 1

| Region and SEQ ID identifier | Amino acid sequence |
|---|---|
| Heavy chain variable region SEQ ID NO: 1 | EVQLVESGGGLVQPGGSLRLSCAASGFTFSDYNMAWVRQAPGKGL EWVATITYEGRNTYYRDSVKGRFTISRDNAKNSLYLQMNSLRAEDT AVYYCASPPQYYEGSIYRLWFAHWGQGTLVTVSS |
| Light chain variable region SEQ ID NO: 2 | AIQLTQSPSSLSASVGDRVTITCRADESVRTLMHWYQQKPGKAPKL LIYLVSNSEIGVPDRFSGSGSGTDFRLTISSLQPEDFATYYCQQTWS DPWTFGQGTKVEIK |
| Heavy Chain SEQ ID NO: 3 | EVQLVESGGGLVQPGGSLRLSCAASGFTFSDYNMAWVRQAPGKGL EWVATITYEGRNTYYRDSVKGRFTISRDNAKNSLYLQMNSLRAEDT AVYYCASPPQYYEGSIYRLWFAHWGQGTLVTVSSASTKGPSVFPLA PSSKSTSGGTAALGCLVKDYFPEPVTVSWNSGALTSGVHTFPAVLQ SSGLYSLSSVVTVPSSSLGTQTYICNVNHKPSNTKVDKKVEPKSCDK THTCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPSRDELTKN QVSLTCLVKGFYPSDIAVEWESNGQPENNYKTTPPVLDSDGSFFLY SKLTVDKSRWQQGNVFSCSVMHEALHNHYTQKSLSLSPG(K)* *The final K may be absent |
| Light chain SEQ ID NO: 4 | AIQLTQSPSSLSASVGDRVTITCRADESVRTLMHWYQQKPGKAPKL LIYLVSNSEIGVPDRFSGSGSGTDFRLTISSLQPEDFATYYCQQTWS DPWTFGQGTKVEIKRTVAAPSVFIFPPSDEQLKSGTASVVCLLNNFY PREAKVQWKVDNALQSGNSQESVTEQDSKDSTYSLSSTLTLSKADY EKHKVYACEVTHQGLSSPVTKSFNRGEC |

Antibody molecules may be typically produced by culturing a host cell containing a vector encoding the antibody sequence under conditions suitable for leading to expression of protein from DNA encoding the antibody molecule of the present invention, and isolating the antibody molecule.

to 10,000 L. Alternatively, bioreactors of a smaller scale such as between 2 L and 100 L may also be used to manufacture an antibody or antibody fragment.

An antibody or antigen-binding fragment thereof is typically found in the supernatant of a mammalian host cell culture, typically a CHO cell culture. For CHO culture processes wherein the protein of interest such as an antibody or antigen-binding fragment thereof is secreted in the supernatant, said supernatant is collected by methods known in the art, typically by centrifugation.

Therefore, the antibody or antigen-binding fragment thereof production method comprises a step of centrifugation and supernatant recovery after cell culture and prior to protein purification. In a further particular embodiment said centrifugation is continuous centrifugation. For avoidance of doubt, supernatant denotes the liquid lying above the sedimented cells resulting from the centrifugation of the cell culture.

Alternatively, host cells are prokaryotic cells, preferably gram-negative bacteria. More preferably, the host cells are E. coli cells. Prokaryotic host cells for protein expression are well known in the art (Terpe, K. Appl Microbial Biotechnol 72, 211-222 (2006)). The host cells are recombinant cells which have been genetically engineered to produce the protein of interest such as an antigen-binding fragment of an antibody. The recombinant E. coli host cells may be derived from any suitable E. coli strain including from MC4100, TG1, TG2, DHB4, DH5α, DH1, BL21, K12, XL1 Blue and JM109. One example is E. coli strain W3110 (ATCC 27,325) a commonly used host strain for recombinant protein fermentations. Antibody fragments can also be produced by culturing modified E. coli strains, for example metabolic mutants or protease deficient E. coli strains.

E. coli host cell cultures (fermentations) may be cultured in any medium that will support the growth of E. coli and expression of the recombinant protein. The medium may be any chemically defined medium such as e.g. described in Durany O, et al. (2004). Studies on the expression of recombinant fuculose-1-phosphate aldolase in Escherichia coli. Process Biochem 39, 1677-1684.

Culturing of the E. coli host cells can take place in any suitable container such as a shake flask or a fermenter depending on the scale of production required. Various large-scale fermenters are available with a capacity of more than 1,000 liters up to about 100,000 liters, Preferably, fermenters of 1,000 to 50,000 liters are used, more preferably 1,000 to 25,000, 20,000, 15,000, 12,000 or 10,000 liters. Smaller scale fermenters may also be used with a capacity of between 0.5 and 1,000 liters.

Other methods for obtaining antigen-binding fragment of a human antibody in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody.

It will be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

The pharmaceutical composition according to the invention as a whole has a pH of from about 4.6 to about 5.5, such as 4.6, 4.7, 4.8, 4.9, 5.0, 5.1, 5.2, 5.3, 5.4 or 5.5. Alternatively, it has a pH of from about 4.6 to about 5.3, such as 4.6, 4.7, 4.8, 4.9, 5.0, 5.1, 5.2 or 5.3. In all the embodiments of the present invention, unless otherwise indicated, the pH value was measured at 23-25° C. and it is within ±0.1 or ±0.2 of a pH unit.

The present invention provides for a method for preparing a pharmaceutical composition comprising an antibody, or an antigen-binding fragment thereof, having a heavy chain variable region comprising SEQ ID NO:1 and a light chain variable region comprising SEQ ID NO:2. The method comprises the steps of preparing a) a low concentration formulation by combining from about 40 mg/ml to about 50 mg/ml of the antibody, or antigen-binding fragment thereof, with a buffer solution comprising glycine and acetate at pH of from about 4.6 to about 5.5; and then b) preparing a high concentration formulation by concentrating the antibody or antigen-binding fragment thereof in the low concentration formulation obtained in a) to a concentration of about 160 mg/ml to 180 mg/ml; and finally c) adding polysorbate 80 to the high concentration formulation obtained in b). Optionally, before step c) the concentration of the antibody or antigen-binding fragment thereof may be adjusted with the buffer solution comprising glycine and acetate.

Additional excipients for use within the pharmaceutical compositions according to the invention include, but are not limited to, viscosity enhancing agents, bulking agents, solubilising agents or combinations thereof.

The present invention also provides for a container comprising the pharmaceutical composition according to the invention. In particular, the container may be, without any limitations, a vial, an ampoule, a tube, a bottle or a syringe (such as a pre-filled syringe) comprising the pharmaceutical composition.

The container may be part of a kit-of-parts comprising one or more containers comprising the pharmaceutical compositions according to the invention and delivery devices such as a syringe, pre-filled syringe, an autoinjector, a needleless device, an implant or a patch, or other devices for parental administration and instructions of use.

In one embodiment of the present invention, a container comprises the pharmaceutical composition comprising:
  a. from about 80 mg/ml to about 200 mg/mL, alternatively from about 120 mg/ml to about 185 mg/ml of antibody, or antigen-binding fragment thereof having:
    i. a heavy chain variable region comprising SEQ ID NO:1 and a light chain variable region comprising SEQ ID NO:2; or
    ii. a heavy chain comprising SEQ ID NO:3 and a light chain comprising SEQ ID NO:4; or
    iii. a heavy chain having at least 80% identity or similarity, preferably 90% identity or similarity to the constant region of the sequence as defined in SEQ ID NO: 3 and a light chain having at least 80% identity or similarity, preferably 90% identity or similarity to the constant region of the sequence as defined in SEQ ID NO: 4.
  b. acetate;
  c. glycine;
  d. polysorbate 80,
wherein the composition has a pH of from about 4.6 to about 5.5.

In one preferred embodiment of the present invention, a container comprises the pharmaceutical composition comprising:
a. about 160 mg/mL of antibody, or antigen-binding fragment thereof having:
  i. a heavy chain variable region comprising SEQ ID NO:1 and a light chain variable region comprising SEQ ID NO:2; or
  ii. a heavy chain comprising SEQ ID NO:3 and a light chain comprising SEQ ID NO:4; or
  iii. a heavy chain having at least 80% identity or similarity, preferably 90% identity or similarity to the constant region of the sequence as defined in SEQ ID NO: 3 and a light chain having at least 80% identity or similarity, preferably 90% identity or similarity to the constant region of the sequence as defined in SEQ ID NO: 4.
b. sodium acetate;
c. glycine;
d. polysorbate 80,
wherein the composition has a pH of about 4.6 to about 5.5.

Also preferably, the present invention provides for a container comprising a pharmaceutical composition obtained by the method according to the present invention, which method comprises the steps of:
a. preparing a low concentration formulation by combining from about 40 mg/ml to about 50 mg/ml of an antibody, or an antigen-binding fragment thereof, having a heavy chain variable region comprising SEQ ID NO:1 and a light chain variable region comprising SEQ ID NO:2 with a buffer solution comprising glycine and acetate at pH of from about 4.6 to about 5.5;
b. preparing a high concentration formulation by concentrating the antibody or antigen-binding fragment thereof of the low concentration formulation obtained in a) to a concentration of about 160 mg/ml to 180 mg/ml;
c. adding polysorbate 80 to the high concentration formulation obtained in b), preferably at from about 0.01 to 0.07% (w/v);
d. optionally, before step c) adjusting the concentration of the antibody or antigen-binding fragment thereof with the buffer solution comprising glycine and acetate.

The pharmaceutical composition obtained by the method of the present invention and comprised in the container has a pH of from about 4.6 to 5.5.

Preferably, the buffer solution comprises from about 20 mM to about 100 mM acetate, preferably from about 40 mM to about 90 mM acetate and from about 140 mM to about 350 mM glycine.

The pharmaceutical compositions or the liquid pharmaceutical formulations according to the invention are for use in therapy.

In one embodiment, the pharmaceutical composition for use in therapy comprises from 80 mg/mL to 200 mg/mL, preferably from about 120 to about 185 mg/mL of an antibody or antigen-binding fragment thereof, acetate, glycine, polysorbate 80, at a pH of from about 4.6 to about 5.5;
wherein the antibody or antigen-binding fragment thereof (as it may apply) comprises:
1) a heavy chain variable region comprising SEQ ID NO: 1 and a light chain variable region comprising SEQ ID NO:2; or
2) a heavy chain comprising SEQ ID NO: 3 and a light chain comprising SEQ ID NO:4; or
3) a heavy chain having at least 80% identity or similarity, preferably 90% identity or similarity to the constant region of the sequence as defined in SEQ ID NO: 3 and a light chain having at least 80% identity or similarity, preferably 90% identity or similarity to the constant region of the sequence as defined in SEQ ID NO: 4;
preferably from about 20 mM to about 100 mM acetate, from about 140 mM to about 350 mM glycine and from about 0.01% to about 0.07% (w/v) polysorbate 80 at a pH of from about 4.6 to about 5.5.

In another embodiment, the pharmaceutical composition for use in therapy is obtained by the method according to the present invention, which method comprises the steps of:
a. preparing a low concentration formulation by combining from about 40 mg/ml to about 50 mg/ml of an antibody, or an antigen-binding fragment thereof, having a heavy chain variable region comprising SEQ ID NO:1 and a light chain variable region comprising SEQ ID NO:2 with a buffer solution comprising glycine and acetate at pH of from about 4.6 to about 5.5;
b. preparing a high concentration formulation by concentrating the antibody or antigen-binding fragment thereof of the low concentration formulation obtained in a) to a concentration of about 160 mg/ml to 180 mg/ml;
c. adding polysorbate 80 to the high concentration formulation obtained in b), preferably at from about 0.01 to 0.07 (w/v) %;
d. optionally, before step c) adjusting the concentration of the antibody or antigen-binding fragment thereof with the buffer solution comprising glycine and acetate.

The pharmaceutical composition according to the invention is also for use in the treatment or prophylaxis of a pathological disorder mediated by IL-17A and/or IL-17F, or that is associated with increased levels of IL-17A and/or IL-17F.

In one embodiment, the pharmaceutical composition for use in the treatment or prophylaxis of a pathological disorder mediated by IL-17A and/or IL-17F, or that is associated with increased levels of IL-17A and/or IL-17F comprises from 80 mg/mL to 200 mg/mL, preferably from about 120 to about 185 mg/mL of an antibody or antigen-binding fragment thereof, acetate, glycine, polysorbate 80, at a pH of from about 4.6 to about 5.5;
wherein the antibody or antigen-binding fragment thereof (as it may apply) comprises:
1) a heavy chain variable region comprising SEQ ID NO: 1 and a light chain variable region comprising SEQ ID NO:2; or
2) a heavy chain comprising SEQ ID NO: 3 and a light chain comprising SEQ ID NO:4; or
3) a heavy chain having at least 80% identity or similarity, preferably 90% identity or similarity to the constant region of the sequence as defined in SEQ ID NO: 3 and a light chain having at least 80% identity or similarity, preferably 90% identity or similarity to the constant region of the sequence as defined in SEQ ID NO: 4;
preferably from about 20 mM to about 100 mM acetate, from about 140 mM to about 350 mM glycine and from about 0.01% to about 0.07% (w/v) polysorbate 80 at a pH of from about 4.6 to about 5.5.

In one preferred embodiment, the pharmaceutical composition for use in the treatment or prophylaxis of a pathological disorder mediated by IL-17A and/or IL-17F, or that is associated with increased levels of IL-17A and/or IL-17F is obtained by the method according to the present invention, which method comprises the steps of:

a. preparing a low concentration formulation by combining from about 40 mg/ml to about 50 mg/ml of an antibody, or an antigen-binding fragment thereof, having a heavy chain variable region comprising SEQ ID NO:1 and a light chain variable region comprising SEQ ID NO:2 with a buffer solution comprising glycine and acetate at pH of from about 4.6 to about 5.5;

b. preparing a high concentration formulation by concentrating the antibody or antigen-binding fragment thereof of the low concentration formulation obtained in a) to a concentration of about 160 mg/ml to 180 mg/ml;

c. adding polysorbate 80 to the high concentration formulation obtained in b), preferably at from about 0.01 to about 0.07 (w/v) %;

d. optionally, before step c) adjusting the concentration of the antibody or antigen-binding fragment thereof with the buffer solution comprising glycine and acetate.

The present invention also provides for the use of the pharmaceutical composition in the manufacture of a medicament for the treatment or prophylaxis of a pathological disorder mediated by IL-17A and/or IL-17F, or that is associated with increased levels of IL-17A and/or IL-17F, wherein the pharmaceutical composition comprises from about 80 mg/mL to about 200 mg/mL, preferably from about 120 to about 180 mg/mL of an antibody or antigen-binding fragment thereof, acetate, glycine, polysorbate 80, at a pH of from about 4.6 to about 5.5;

wherein the antibody or antigen-binding fragment thereof (as it may apply) comprises:
1) a heavy chain variable region comprising SEQ ID NO: 1 and a light chain variable region comprising SEQ ID NO:2; or
2) a heavy chain comprising SEQ ID NO: 3 and a light chain comprising SEQ ID NO:4; or
3) a heavy chain having at least 80% identity or similarity, preferably 90% identity or similarity to the constant region of the sequence as defined in SEQ ID NO: 3 and a light chain having at least 80% identity or similarity, preferably 90% identity or similarity to the constant region of the sequence as defined in SEQ ID NO: 4;

preferably from about 20 mM to about 100 mM sodium acetate, from about 140 mM to about 350 mM glycine and from about 0.01 to about 0.07 (w/v) % polysorbate 80 at a pH of from about 4.6 to about 5.5.

In one preferred embodiment, the use of the pharmaceutical composition in the manufacture of a medicament for the treatment or prophylaxis of a pathological disorder mediated by IL-17A and/or IL-17F, or that is associated with increased levels of IL-17A and/or IL-17F, wherein the pharmaceutical composition is obtained by the method according to the present invention, which method comprises the steps of:

a. preparing a low concentration formulation by combining from about 40 mg/ml to about 50 mg/ml of an antibody, or an antigen-binding fragment thereof, having a heavy chain variable region comprising SEQ ID NO:1 and a light chain variable region comprising SEQ ID NO:2 with a buffer solution comprising glycine and acetate at pH of from about 4.6 to about 5.5;

b. preparing a high concentration formulation by concentrating the antibody or antigen-binding fragment thereof of the low concentration formulation obtained in a) to a concentration of about 160 mg/ml to 180 mg/ml;

c. adding polysorbate 80 to the high concentration formulation obtained in b), preferably at from about 0.01 to about 0.07 (w/v) %;

d. optionally, before step c) adjusting the concentration of the antibody or antigen-binding fragment thereof with the buffer solution comprising glycine and acetate.

Also contemplated by the present invention is a method of treating or preventing a pathological disorder mediated by IL-17A and/or IL-17F, or that is associated with increased levels of IL-17A and/or IL-17F in a mammalian subject comprising administering pharmaceutical composition comprising from about 80 mg/mL to about 200 mg/mL, preferably from about 120 to about 185 mg/mL of an antibody or antigen-binding fragment thereof, acetate, glycine, polysorbate 80, at a pH of from about 4.6 to about 5.5;

wherein the antibody or antigen-binding fragment thereof (as it may apply) comprises:
1) a heavy chain variable region comprising SEQ ID NO: 1 and a light chain variable region comprising SEQ ID NO:2; or
2) a heavy chain comprising SEQ ID NO: 3 and a light chain comprising SEQ ID NO:4; or
3) a heavy chain having at least 80% identity or similarity, preferably 90% identity or similarity to the constant region of the sequence as defined in SEQ ID NO: 3 and a light chain having at least 80% identity or similarity, preferably 90% identity or similarity to the constant region of the sequence as defined in SEQ ID NO: 4;

preferably from about 20 mM to about 100 mM acetate, from about 150 mM to about 250 mM glycine and from about 0.01 to about 0.07 (w/v) % polysorbate 80 at a pH of from about 4.6 to about 5.5.

Preferably; the pathological disorder is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury; pelvic inflammatory disease, Alzheimer's Disease, Crohn's disease, inflammatory bowel disease, irritable bowel syndrome, Ulcerative colitis, Castleman's disease, ankylosing spondylitis, axial spondyloarthritis and other spondyloarthropathies, dermatomyositis, myocarditis, uveitis, exophthalmos, autoimmune thyroiditis; Peyronie's Disease, coeliac disease, gallbladder disease, Pilonidal disease, peritonitis, psoriasis, atopic dermatitis, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis and hypochlorhydria.

More preferably, the pathological disorder is selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, Crohn's disease, ulcerative colitis, ankylosing spondylitis, axial spondyloarthritis and other spondyloarthropathies; and even more preferably the pathological disorder is selected from the group consisting of rheumatoid arthritis, psoriasis, psoriatic arthritis, Crohn's disease, ulcerative colitis, ankylosing spondylitis and axial spondyloarthritis.

Even more preferably, the pathological disorder is selected is selected from the group consisting of rheumatoid arthritis, Crohn's disease, ulcerative colitis, psoriasis, psoriatic arthritis, ankylosing spondylitis, and axial spondyloarthritis.

In one preferred embodiment of the present invention, the pharmaceutical composition is for use in the treatment or prophylaxis of rheumatoid arthritis, Crohn's disease, ulcerative colitis, psoriasis, psoriatic arthritis, ankylosing spondylitis and axial spondyloarthritis and comprises about 160 mg/mL of an antibody or antigen-binding fragment thereof, acetate, glycine, polysorbate 80, at a pH of from about 4.6 to about 5.5;

wherein the antibody or antigen-binding fragment thereof (as it may apply) comprises:
1) a heavy chain variable region comprising SEQ ID NO: 1 and a light chain variable region comprising SEQ ID NO:2; or
2) a heavy chain comprising SEQ ID NO: 3 and a light chain comprising SEQ ID NO:4; or
3) a heavy chain having at least 80% identity or similarity, preferably 90% identity or similarity to the constant region of the sequence as defined in SEQ ID NO: 3 and a light chain having at least 80% identity or similarity, preferably 90% identity or similarity to the constant region of the sequence as defined in SEQ ID NO: 4.

In another preferred embodiment, the pharmaceutical composition is for use in the treatment or prophylaxis of rheumatoid arthritis, Crohn's disease, ulcerative colitis psoriasis, psoriatic arthritis, ankylosing spondylitis and axial spondyloarthritis, wherein the pharmaceutical composition is obtained by the method according to the present invention, which method comprises the steps of:
a. preparing a low concentration formulation by combining from about 40 mg/ml to about 50 mg/ml of an antibody, or an antigen-binding fragment thereof, having a heavy chain variable region comprising SEQ ID NO:1 and a light chain variable region comprising SEQ ID NO:2 with a buffer solution comprising glycine and acetate at pH of from about 4.6 to about 5.5;
b. preparing a high concentration formulation by concentrating the antibody or antigen-binding fragment thereof of the low concentration formulation obtained in a) to a concentration of about 160 mg/ml to 180 mg/ml;
c. adding polysorbate 80 to the high concentration formulation obtained in b), preferably at from about 0.01 to about 0.07 (w/v)%;
d. optionally, before step c) adjusting the concentration of the antibody or antigen-binding fragment thereof with the buffer solution comprising glycine and acetate.

The pharmaceutical composition according to the invention may be administered in a therapeutically effective amount. The term "therapeutically effective amount" as used herein refers to an amount of a therapeutic agent (i.e. an antibody) needed to treat, ameliorate or prevent a targeted disease, disorder or condition, or to exhibit a detectable therapeutic, pharmacological or preventative effect. For any antibody or antigen-binding fragments thereof, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount of antibody will be from 0.01 mg/kg to 500 mg/kg, for example 0.1 mg/kg to 200 mg/kg or 1 to 100 mg/kg.

For the treatment of the above diseases and/or disorders, the appropriate dosage will vary depending upon, for example, the particular antibody to be employed, the subject treated, the mode of administration and the nature and severity of the condition being treated. In a particular embodiment, the pharmaceutical composition according to the invention is administered by intravenous or subcutaneous route. When administered via intravenous injection, it may be administered as a bolus injection or as a continuous infusion. The pharmaceutical composition according to any of the embodiments of the invention may also be administered by intramuscular injection. The pharmaceutical composition may be injected using a syringe, an injection device such as an autoinjector, a needleless device, an implant and a patch.

The liquid pharmaceutical formulation of the invention is suitably administered to the patient at one time or over a series of treatments and may be administered to the patient at any time from diagnosis onwards; it may be administered as the sole treatment or in conjunction with other drugs or therapies useful in treating the conditions as described herein before.

The antibody or antigen-binding fragment thereof may be the sole active ingredient in the liquid pharmaceutical formulation. Alternatively, the antibody or antigen-binding fragment thereof may be administered in combination, e.g. simultaneously, sequentially or separately, with one or more other therapeutically active ingredients. Active ingredient as employed herein refers to an ingredient with a pharmacological effect, such as a therapeutic effect, at a relevant dose. In some embodiments the antibody or antigen-binding fragment thereof in the pharmaceutical composition may be accompanied by other active ingredients including other antibodies or non-antibody ingredients, administered by the same or by a different route of administration, to treat other inflammatory or autoimmune diseases. In one embodiment, the subject is administered, simultaneously or in sequence (before and/or after) other antibody ingredients, such as anti-TNF antibodies or non-antibody ingredients such as small molecule drug molecules.

The invention will now be further described by way of examples with references to embodiments illustrated in the accompanying drawings

EXAMPLES

Abbreviations

Anti-IL-17A/F Ab: anti IL-17A and IL-17F antibody having sequences as defined in SEQ ID NOs: 3 and 4 of Table 1; AFT: Accelerated Freeze/thaw; BPP: Biologics Pilot Plant; CCPS: Cell Culture Process Sciences; CEX-HPLC: Cation Exchange Chromatography—High Pressure Liquid Chromatography; cIEF: capillary Isoelectric Focusing; DSL: dynamic light scattering; DFS: differential scanning fluorimetry; DPS: Downstream Process Sciences; DTT: Dithiothreitol; FZT: Freeze/thaw; HMW: Heavy Molecular Weight; H PLC: high pressure liquid chromatography; HSC: High throughput Self-interaction Chromatography; IAA: Iodoacetamide ICE: Imaged Capillary Electrophoresis; LMW: Low Molecular Weight; MW: Molecular Weight; NP: Not available; PCR: polymerase chain reaction; PEG: Poly Ethylene Glycol; PES: Poly Ether Sulfone; P520: Polysorbate 20; P580: Polysorbate 80; PTFE: Polytetrafluoroethylene; PVDF: Polyvinylidene fluoride; RH: relative humidity; % RSD: % Relative Standard Deviation; SDS-PAGE: Sodium Dodecyl Sulphate—Polyacrylamide Gel Electrophoresis; s: Seconds; SEC: Size Exclusion Chromatography; SEC—HPLC: Size Exclusion Chromatography—High Pressure Liquid Chromatography; SIC: Self-Interaction Chromatography; Trp: Tryptophan; WFI: Water for Injection; w/v: weight/volume.

Example 1: Additives Screening

Initial screening studies were performed by interrogating the effect of different additives on the anti-IL-17A and IL-17F antibody at 1 mg/mL by determining the B22 (second viral coefficient) value by SIC and selecting 5 top formulations with the greatest likelihood of success (HSC™ Technology). Positive values of B22 suggest which additive may help mitigating more effectively protein-protein interactions that can lead to aggregation and other types of degradation in a formulation comprising the Anti-IL-17A/F Ab.

Different additives were screened. The top additives returning the highest B22 values while not harming the conformational stability of the antibody were identified. From an incomplete factorial design of the possible combinations of the best 9 additives and 3 buffer systems a total of 36 formulations were generated and the resulting B22 values were measured through the HSC™ Technology (Soluble Therapeutics™).

From the analysis of these 36 formulations, 5 formulations (Table 2) were predicted and validated though SIC (data not shown). In Table 2, M means measured B22 value and C means calculated B22 value

TABLE 2

| | | | | | M | C |
|---|---|---|---|---|---|---|
| 1 | 0.04M Citrate pH 5.5 | 3 mM KH2PO4 | 1.5% (w/v) PEG3350 | | 3.8 | 3.6 |
| 2 | 0.04M Citrate pH 5.5 | 50 mM K2HPO4 | 35 uM PS20 | 75 mM Sucrose | 3.5 | 3.4 |
| 3 | 0.04M Acetate pH 5.7 | 15 mM NaOAc | 0.1% (w/v) Benzyl Alcohol | 100 mM Sucrose | 2.9 | 2.7 |
| 4 | 0.04M Citrate pH 5.5 | 25 mM K2HPO4 | 17.5 uM PS20 | 100 mM Sucrose | 2.8 | 2.5 |
| 5 | 0.04M Acetate pH 5.7 | 25 mM K2HPO4 | 125 mM Sucrose | | 2.8 | 2.4 |

Example 2: Effect of High Concentration of Antibody on Best Performing Formulations The results of the study performed in Example 1, performed with the Anti-IL-17A/F Ab at 1 mg/ml, were subsequently verified at concentration of about 160 mg/ml of Anti-IL-17A/F Ab and were found not to be representative.

The formulations which were included in the screen were (Table 3):

TABLE 3

| 1 | 40 mM Sodium Citrate pH 5.6 | 3 mM KH2PO4 | 1.5% (w/v) PEG 3350 | |
|---|---|---|---|---|
| 2 | 40 mM Sodium Citrate pH 5.6 | 50 mM K2HPO4 | 75 mM Sucrose | 0.00044% (w/v) PS20 |
| 3 | 40 mM Sodium Acetate pH 5.7 | 15 mM NaOAc | 100 mM Sucrose | 0.1% (w/v) Benzyl Alcohol |
| 4 | 40 mM Sodium Citrate pH 5.5 | 25 mM K2HPO4 | 100 mM Sucrose | 0.00022% (w/v) PS20 |
| 5 | 40 mM Sodium Acetate pH 5.7 | 25 mM K2HPO4 | 125 mM Sucrose | |
| 6 | 40 mM Sodium Citrate pH 5.5 | 50 mM K2HPO4 | 6 mM Histidine | |

The Anti-IL-17A/F Ab at 88.7 mg/mL in 20 mM Histidine, 250 mM Sorbitol pH6.0 was concentrated using vivaflow 50 cassettes with a MWCO of 30 kDa PES membrane. Antibody loss was observed and to account for this predicted loss, the antibody was concentrated up to 175 mg/mL before exchanging the buffer into the relevant formulation buffers using PD10 columns containing Sephadex G-25 medium.

After buffer exchange the final formulations were adjusted to 160 mg/mL using the relevant formulation buffers (Table 3—formulations 1 to 6); the amounts are negligible and do not affect the concentration of buffer components). Following this adjustment, PS20 was spiked into formulations 2 and 4 to reach a final content of 0,00044 and 0.00022% (w/v) respectively and benzyl alcohol was spiked into formulation 3 to reach a final content of 0.1% (w/v).

Under a laminar flow hood, formulations 1 to 6 were transferred into 2 mL 96 deep well plate then sub-aliquoted into twenty sterile 96-well half area plates (80 µL per well). One mL of each formulation was also transferred into sterile 2 mL Schott Type I Glass vials sealed with Flurotec coated Westar rubber stoppers and Tru-Edge Flip off seals for initial testing.

The plates were stored as the following (Table 4; a: 2 mL Schott vials—remaining in 96-well plate; b: only for formulation 1; c: for formulations 2-6; d: for formulation 2-6 this measurement was taken at 5 weeks):

TABLE 4

| | Time points in weeks | | | | | | |
|---|---|---|---|---|---|---|---|
| Conditions | Initial | 2 weeks | 4 weeks | 6 weeks | 8 weeks | 12 weeks | Spares |
| 5° C. | ✓[a] | ✓ | ✓ | ✓[c] | ✓ | ✓ | ✓ |
| 25° C./60% RH | | ✓ | ✓ | ✓[c] | ✓ | ✓ | ✓ |
| 35° C./75% RH | | ✓ | ✓ | ✓[c] | ✓ | ✓ | ✓ |
| FZT | | | ✓[b] | | ✓[c] | | |
| AFT | ✓[b] | | ✓[c, d] | | | | |

The Freeze/thaw stress was performed by freezing/thawing the formulation five times using a Cryomed Controlled rate freezer with freezing and thawing rates set at 0.5° C./min for the low rate freeze/thaw experiment (FZT) and 2° C./min for the accelerated rate freeze/thaw experiment (AFT). In each case, the probe of the freezer was inserted in the well of an additional plate containing a water/glycerol solution of similar viscosity to the samples. The FZT analysis was performed after 4 weeks at 5° C. for formulation 1 whilst it was performed after 8 weeks at 5° C. for formulations 2 to 6. The AFT analysis was performed after 1 week at 5° C. for formulation 1 and after 5 weeks at 5° C. formulations 2 to 6.

Visual Assessment

The plates were scanned using an Epson Scanner Expression v750 Pro model J221A in colour (1200 dpi, 24 bits, no image treatment) and greyscale (1200 dpi, 16 bits, no image treatment). Automated visual inspection scan was performed using the Molecular Devices M5 plate reader performing a 1 point well scan measuring absorbance at 600 nm.

By visual inspection, for all time points and conditions formulation 1 always looked more turbid than all remaining formulations. By A600, at all conditions formulations 1 and 2 seem to show an increase in absorbance at 600 nm (Table 8) however the increase was minor. After FZT and AFT stress, formulation 1 shows an increase in absorbance at 600 nm (Table 5) with the increase being less pronounced after AFT stress.

TABLE 5

| Conditions | Time point in weeks | Formulations | | | | | |
|---|---|---|---|---|---|---|---|
| | | 1 | 2 | 3 | 4 | 5 | 6 |
| 5° C. | Tinitial | 0.10 | 0.09 | 0.08 | 0.12 | 0.10 | 0.13 |
| | T04 | 0.12 | 0.20 | 0.09 | 0.12 | 0.08 | 0.10 |
| | T08 | 0.16 | 0.20 | 0.13 | 0.11 | 0.08 | 0.10 |
| | T12 | NP$^a$ | 0.21 | 0.019 | 0.08 | 0.08 | 0.09 |
| 25° C./ 60% RH | Tinitial | 0.10 | 0.09 | 0.08 | 0.12 | 0.10 | 0.13 |
| | T04 | 0.27 | 0.15 | 0.09 | 0.09 | 0.10 | 0.07 |
| | T08 | 0.10 | 0.24 | 0.18 | 0.15 | 0.15 | 0.09 |
| | T12 | NP$^a$ | 0.24 | 0.12 | 0.11 | 0.15 | 0.09 |
| 35° C./ 75% RH | Tinitial | 0.10 | 0.09 | 0.08 | 0.12 | 0.10 | 0.13 |
| | T04 | 0.19 | 0.16 | 0.14 | 0.10 | 0.10 | 0.08 |
| | T08 | 0.16 | 0.19 | 0.11 | 0.25 | 0.15 | 0.11 |
| | T12 | NP$^a$ | 0.22 | 0.15 | 0.17 | 0.14 | 0.11 |
| FZT | Tinitial | 0.10 | 0.09 | 0.08 | 0.12 | 0.10 | 0.13 |
| | T04 | 0.25 | — | — | — | — | — |
| | T08 | — | 0.21 | 0.12 | 0.13 | 0.09 | 0.11 |
| AFT | Tinitial | 0.10 | 0.09 | 0.03 | 0.12 | 0.10 | 0.13 |
| | T04 | 0.15 | 0.20 | 0.11 | 0.14 | 0.10 | 0.10 |

Protein Concentration Determination by UV at 280 nm

Samples were diluted to a nominal concentration of 20 mg/mL then to a nominal concentration of 0.5 mg/mL with filtered de-ionized water. The concentration was determined using absorbance at 280 nm combined with a standard curve in a flat bottom UV transparent 96-well plate with an extinction coefficient of 1.56 mL/(mg*cm) using a Molecular devices M5 plate reader (sample volume: 100 µL).

No obvious decreasing or increasing trends can be observed in this data over the course of the study (Table 6A).

TABLE 6A

| Conditions | Time point in weeks | Formulations | | | | | |
|---|---|---|---|---|---|---|---|
| | | 1 | 2 | 3 | 4 | 5 | 6 |
| 5° C. | Tinitial | 162.8 | 171.1 | 170.5 | 168.7 | 174.8 | 169.2 |
| | T04 | 159.0 | 196.2 | 208.4 | 193.6 | 195.8 | 192.2 |
| | T08 | 150.9 | 177.7 | 191.8 | 169.9 | 179.0 | 178.1 |
| | T12 | — | 141.9 | 158.9 | 136.8 | 144.5 | 150.9 |
| 25° C./ 60% RH | Tinitial | 162.8 | 171.1 | 170.5 | 168.7 | 174.8 | 169.2 |
| | T04 | 162.9 | 196.1 | 206.0 | 189.6 | 210.9 | 185.3 |
| | T08 | 165.6 | 189.1 | 203.1 | 177.1 | 196.4 | 180.8 |
| | T12 | — | 195.1 | 162.9 | 152.6 | 197.8 | 165.6 |
| 35° C./ 75% RH | Tinitial | 162.8 | 171.1 | 170.5 | 168.7 | 174.8 | 169.2 |
| | T04 | 169.1 | 195.0 | 217.5 | 192.9 | 205.0 | 181.4 |
| | T08 | 168.8 | 208.4 | 191.4 | 182.0 | 200.0 | 211.6 |
| | T12 | — | 184.3 | 163.2 | 160.0 | 186.2 | 168.8 |
| FZT | Tinitial | 162.8 | 171.1 | 170.5 | 168.7 | 174.8 | 169.2 |
| | T04 | 160.1 | — | — | — | — | — |
| | T08 | — | 176.5 | 188.9 | 175.8 | 187.0 | 182.7 |
| AFT | Tinitial | 162.8 | 171.1 | 170.5 | 168.7 | 174.8 | 169.2 |
| | T04 | 169.2 | 177.2 | 183.0 | 177.3 | 176.2 | 178.8 | pH Measurement

The pH was determined on a Mettler Toledo S47 pH meter at 23-25° C. No dilution was performed prior to the measurement.

For samples stored at 5° C., during the course of the study the pH value for all formulations was within 0.2 pH unit of the initial value (Table 6B).

TABLE 6B

| | Buffers | | | | | |
|---|---|---|---|---|---|---|
| | 1A | 2 | 3 | 4 | 5 | 6 |
| | 5.57 | 5.55 | 5.75 | 5.49 | 5.70 | 5.53 |

| Conditions | Time point in weeks | Formulations | | | | | |
|---|---|---|---|---|---|---|---|
| | | 1 | 2 | 3 | 4 | 5 | 6 |
| 5° C. | Tinitial | 5.56 | 5.55 | 5.89 | 5.51 | 5.76 | 5.56 |
| | T04 | 5.60 | 5.54 | 5.92 | 5.54 | 5.76 | NP$^a$ |
| | T08 | 5.74 | 5.56 | 5.90 | 5.58 | 5.77 | 5.57 |
| | T12 | NP$^b$ | 5.55 | 5.91 | 5.69 | 5.76 | 5.55 |
| 25° C./ 60% RH | Tinitial | 5.56 | 5.55 | 5.89 | 5.51 | 5.76 | 5.56 |
| | T04 | 8.39 | 5.55 | 5.88 | 5.89 | 5.76 | 5.49 |
| | T08 | 8.17 | 5.63 | 5.96 | 6.07 | 5.79 | 5.68 |
| | T12 | NP$^b$ | NP$^a$ | 5.96 | 6.56 | NP$^a$ | NP$^a$ |
| 35° C./ 75% RH | Tinitial | 5.56 | 5.55 | 5.89 | 5.51 | 5.76 | 5.56 |
| | T04 | 7.48 | 5.55 | 5.90 | 6.50 | 5.76 | 5.58 |
| | T08 | 8.66 | 5.71 | 6.00 | NP$^a$ | 5.87 | 5.90 |
| | T12 | NP$^b$ | NP$^a$ | 6.44 | 8.25 | NP$^a$ | 5.62 |
| FZT | Tinitial | 5.56 | 5.55 | 5.89 | 5.51 | 5.76 | 5.56 |
| | T04 | 5.56 | — | — | — | — | — |
| | T08 | — | 5.55 | 5.90 | 5.60 | 5.78 | 5.57 |
| AFT | Tinitial | 5.56 | 5.55 | 5.89 | 5.51 | 5.76 | 5.56 |
| | T04 | 5.58 | 5.56 | 5.89 | 5.59 | 5.77 | 5.57 |

$^a$No sample remaining in the plate;
$^b$formulation 1 had to be re-prepared impairing time collection at T12.

For formulation 3, the initial value was 0.14 higher than the buffer alone value which suggests that in this buffer the antibody drives the pH value up. Formulations 1 and 4, even though the pH is within 0.2 pH unit of initial, there seems to be a trend showing a gradual increase over 2 and 3 months respectively which is not observed in the other formulations. For samples stored at 25° C., during the course of the study, the pH value for formulations 2, 3, 5 and 6 was within 0.2 pH unit with 2, 5 and 6 not being able to be determined due to no remaining sample at T12. For samples stored at 25° C., for formulations 1 and 4 a significant increase in pH can be observed from T04 onwards at 25° C. and 35° C. suggesting a degradation of the sample or contamination. For samples stored at 35° C., formulations 2, 5 and 6 display pH values within 0.2 pH unit of initial with an out of trend value observed at T08 for formulation 6. As no sample was remaining for measurement at T12 for formulations 2 and 5 no conclusions can be drawn regarding possibility of an increase in pH over time as values are still within 0.2 pH unit of initial. Formulation 3 at T12 shows an abnormal increase in pH.

Size Exclusion Chromatography

Analyses were performed on sample aliquots diluted to 5 mg/mL in filtered mobile phase (0.2 M Na Phosphate pH7.0) using Agilent 1200 series HPLC with 96-well plate autosampler.

Analyses were performed as follows:
Sample load: 50 µL (250 µg) at 5 mg/mL
Column: Tosoh BioScience TSK Gel G3000 SWXL, 250 Å, 5 µm, 7.8×300 mm (part number: 8541)
Eluent A: 0.2 M Sodium Phosphate, pH7.0
Flow rate: 1 mL/min
Detection: UV (Wavelength: 280 nm, Resolution: 8 nm, reference: off)
Column Temperature: 25° C.
Sample Temperature: 4° C.
Gradient: Isocratic
Max Pressure: 70 bar
Run time: 15 min
Post time: 5 min Data analysis was performed using Empower 2 software.

The % increase of HMW species by SEC for formulation 1 to 6 in comparison to reference formulations DS (anti-IL-17A/F Ab at 80 mg/ml in 20 mM histidine, 250 mM Sorbitol, 0.02% Polysorbate 80, pH 6.0) and DP (same as DS but packaged in a glass vial) is shown in Table 7.

For samples stored at 5° C., after 12 weeks, formulations 2, 4, 5 and 6 show a similar degree of aggregation than the DS and DP formulations, with formulation 3 showing a higher increase in aggregation than the DS and DP formulations. Generation of fragments is minimal for formulations 2, 3, 5 and 6 (data not shown).

For samples stored at 25° C., formulation 3 was the best performer however all formulations perform worse than the DS and DP formulations. All formulations showed an increase in fragmentation levels with formulations (data not shown). Formulation 2 shows a decrease in % HMW species over the 12 weeks and a significant increase in fragmentation.

For samples stored at 35° C., formulation 6 was the best performer, however all formulations perform worse than the DS and DP formulations. All formulations show an increase in fragmentation levels (data not shown).

TABLE 1

| Conditions | Formulations | Time points in weeks | | |
|---|---|---|---|---|
| | | T04 | T08 | T12 |
| 5° C. | 1 | 0.21 | 0.36 | NP |
| | 2 | 0.22 | 0.18 | 0.44 |
| | 3 | 0.62 | 0.59 | 1.03 |
| | 4 | 0.14 | 0.06 | 0.31 |
| | 5 | 0.38 | 0.38 | 0.62 |
| | 6 | 0.12 | 0.16 | 0.38 |
| | DS | 0.20 | 0.50 | 0.70 |
| | DP | 0.00 | 0.20 | 0.40 |
| 25° C./60% RH | 1 | 3.88 | 3.04 | NP |
| | 2 | 1.00 | 0.76 | −0.36 |
| | 3 | 1.87 | 2.23 | 2.47 |
| | 4 | 1.58 | 2.56 | 4.64 |
| | 5 | 1.71 | 2.09 | 3.09 |
| | 6 | 1.13 | 1.39 | 1.93 |
| | DS | 0.80 | 1.30 | 1.70 |
| | DP | 0.40 | 0.90 | 1.30 |

TABLE 1-continued

| Conditions | Formulations | Time points in weeks | | |
|---|---|---|---|---|
| | | T04 | T08 | T12 |
| 35° C./75% RH | 1 | 3.44 | 4.66 | NP |
| | 2 | 2.21 | 2.49 | 3.29 |
| | 3 | 3.49 | 3.70 | 4.59 |
| | 4 | 4.75 | 6.41 | 7.82 |
| | 5 | 3.15 | 4.19 | 5.11 |
| | 6 | 2.08 | 3.06 | 3.19 |
| 40° C./75% RH | DP | 1.60 | 2.60 | 3.80 | iCE

Imaged Capillary Electrophoresis was performed using a Protein Simple iCE3 system.

Analyses were Performed as Follows:

Formulations 1 to 6 were diluted to a nominal concentration of 20 mg/mL then to a concentration of 2 mg/mL (using the concentration determined by A280) with filtered de-ionized water. Analyses were performed on samples at 0.2 mg/mL (1/10 dilution in master mix of the samples at 2 mg/mL). A master mix with the following components was prepared (Table 8):

TABLE 8

| DI water | 1% MC | Pharmalytes 3-10 | pI marker 4.65 | pI marker 9.50 |
|---|---|---|---|---|
| 100 µL | 70 µL | 8 µL | 1 µL | 1 µL |

The focus parameters were as follows: 1 min at 1500 Volts followed by 6 min at 3000 Volts.

The results are reported in Table 9A (% acidic species) and Table 9B (% basic species). At 5° C., no significant changes in % acidic species can be observed across the conditions and formulations with values all within 2-3%.

For samples stored at 25° C., an increase in % acidic species can be observed for all formulations over 12 weeks with formulations 1 and 4 showing a significant increase. This observation is likely linked to the increase in pH observed in those 2 formulations after initial mixing.

For samples stored at 35° C., a significant increase in % acidic species is observed after initial mixing and subsequent time points for all formulations with formulation 4 showing the most increase over 12 weeks. Freeze/thaw stress does not affect the % of acidic species in any formulations.

With respect to the % basic species, at 5° C., there were no significant changes observed across the formulations and time points.

For samples stored at 25° C., formulations 3, 5 and 6 show a slight increase in % basic species over time with formulations 1 and 4 showing a more significant increase in basic species (ca. 2.5%).

For samples stored at 35° C., all formulations show an increase in % basic species with formulation 3 showing the lowest increase. Freeze/thaw stress did not affect the % of basic species in any formulations.

TABLE 9A

| Conditions | Time point in weeks | Formulations | | | | | |
|---|---|---|---|---|---|---|---|
| | | 1 | 2 | 3 | 4 | 5 | 6 |
| 5° C. | Tinitial | 59.80 | 57.39 | 57.11 | 57.72 | 57.56 | 56.63 |
| | T04 | 56.69 | 58.42 | 59.06 | 57.82 | 60.45 | 59.30 |
| | T08 | 60.09 | 57.26 | 57.35 | 58.14 | 59.81 | 56.38 |
| | T12 | NP[a] | 59.70 | 59.37 | 59.76 | 59.71 | 59.02 |
| 25° C./ 60% RH | Tinitial | 59.80 | 57.39 | 57.11 | 57.72 | 57.56 | 56.63 |
| | T04 | 65.12 | 61.26 | 59.99 | 65.11 | 60.12 | 60.46 |
| | T08 | 68.07 | 63.38 | 59.99 | 69.52 | 60.05 | 62.35 |
| | T12 | NP[a] | 55.16 | 62.37 | 75.95 | NP[b] | 63.55 |
| 35° C./ 75% RH | Tinitial | 59.80 | 57.39 | 57.11 | 57.72 | 57.56 | 56.63 |
| | T04 | 68.20 | 67.65 | 64.48 | 69.15 | 64.39 | 66.34 |
| | T08 | 67.79 | 71.74 | 67.76 | 79.29 | 68.77 | 71.24 |
| | T12 | NP[a] | 75.11 | 71.43 | 87.65 | NP[b] | 83.81 |
| FZT | Tinitial | 59.80 | 57.39 | 57.11 | 57.72 | 57.56 | 56.63 |
| | T04 | 57.21 | — | — | — | — | — |
| | T08 | — | 57.83 | 58.71 | 58.02 | 58.00 | 57.93 |
| AFT | Tinitial | 59.80 | 57.39 | 57.11 | 57.72 | 57.56 | 56.63 |
| | T04 | 58.32 | 57.41 | 57.63 | 57.87 | 57.55 | 58.14 |

[a]not available
[b]no sample remaining to be tested

TABLE 9B

| Conditions | Time point in weeks | Formulations | | | | | |
|---|---|---|---|---|---|---|---|
| | | 1 | 2 | 3 | 4 | 5 | 6 |
| 5° C. | Tinitial | 2.67 | 2.23 | 2.34 | 2.15 | 2.16 | 2.28 |
| | T04 | 2.42 | 2.53 | 2.62 | 2.76 | 2.83 | 2.83 |
| | T08 | 2.97 | 2.25 | 2.19 | 2.70 | 2.10 | 2.53 |
| | T12 | NP[a] | 2.77 | 2.19 | 2.45 | 2.41 | 2.44 |
| 25° C./ 60% RH | Tinitial | 2.67 | 2.23 | 2.34 | 2.15 | 2.16 | 2.28 |
| | T04 | 3.20 | 3.28 | 3.04 | 3.59 | 3.27 | 3.49 |
| | T08 | 5.24 | 3.92 | 2.90 | 4.34 | 3.10 | 2.42 |
| | T12 | NP[a] | 18.61 | 2.89 | 4.80 | NP[b] | 2.90 |
| 35° C./ 75% RH | Tinitial | 2.67 | 2.23 | 2.34 | 2.15 | 2.16 | 2.28 |
| | T04 | 3.64 | 4.29 | 3.56 | 3.64 | 4.00 | 4.10 |
| | T08 | 5.21 | 4.75 | 3.53 | 5.48 | 4.20 | 4.14 |
| | T12 | NP[a] | 6.09 | 3.40 | 5.02 | NP[b] | 5.13 |
| Slow FZT | Tinitial | 2.67 | 2.23 | 2.34 | 2.15 | 2.16 | 2.28 |
| | T04 | 2.48 | — | — | — | — | — |
| | T08 | — | 2.51 | 2.39 | 3.16 | 2.26 | 2.69 |
| Fast FZT | Tinitial | 2.67 | 2.23 | 2.34 | 2.15 | 2.16 | 2.28 |
| | T04 | 2.37 | 2.63 | 2.49 | 2.28 | 2.36 | 2.24 |

[a]not available
[b]no sample remaining to be tested

Intrinsic Fluorescence

Analysis was performed on 100 μL of sample from each formulation at 0.5 mg/mL of antibody. This method is based upon the intrinsic fluorescent properties of Trp. Trp is known to fluoresce strongly at 340 nm when excited at 280 nm and shielded from water; Trp exposed to water fluoresces weakly. This property can be used to assess the stability of proteins, as the protein begins to unfold the shielded Trp's are exposed to water resulting in a reduction in fluorescence, as proteins aggregate more Trp's are shielded the fluorescence should increase. The method was carried out in a flat bottom 96-well opaque black fluorescence plate using the molecular devices M5 plate reader (read from top, no shake) with an excitation wavelength of 280 nm and an emission wavelength of from 310 nm to 370 nm with 6 flashes per read. The blank plate was water and the reference standard was 5× Reference standard at 0.5 mg/mL. The results were normalized for concentration against the reference standard and reported as a response factor (Table 11) using the following calculation:

((FLU/Concentration)/FLU Reference Standard)*100

At 5° C., over 12 weeks, formulations 2 and 3 show less of an increase of the response factor than formulations 4, 5 and 6 suggesting that the molecule is less susceptible to aggregation for formulations 2 and 3 (Table 10). For all formulations 2 to 6 there is a significant increase at T04 which is also observed at the other conditions. A possible explanation for this could be increased susceptibility to aggregation in all formulations 2 to 6 after 1 month which would be reversible (non-covalent aggregation) as the effect is much less pronounced for subsequent time points. However, as the effect is similar across the conditions and we would expect to see less of an effect at lower temperatures, this observation seems to be an outlier as all measurements at T04 are higher. This could also be linked to an error in the preparation or measurement.

At 25° C., over 12 weeks formulation 2 shows the least increase in response factor compared to formulations 3, 4, 5 and 6 suggesting that the molecule is less susceptible to aggregation for this formulation.

At 35° C., over 12 weeks, formulations 2 and 4 show the least increase in response factor compared to formulations 3, 5 and 6 suggesting that the molecule is less susceptible to aggregation for formulations 2 and 4.

After slow and fast freeze/thaw stress, formulations 2, 4 and 6 show less of an increase of the response factor than formulations 3 and 5 suggesting that the molecule is less susceptible to aggregation for formulations 2, 4 and 6.

In the case of formulation 1, the response factor decreases after slow and fast freeze/thaw stress as well as after 12 weeks at all conditions, which could be linked to unfolding of the protein in this formulation.

To be noted that it is not known at which point the magnitude of change of the response factor becomes significant in order to differentiate between formulations. Consequently, it is difficult to judge performance of the formulations based on intrinsic fluorescence only as it does not correlate with the SEC data.

TABLE 10

| Conditions | Time point in weeks | Formulations | | | | | |
|---|---|---|---|---|---|---|---|
| | | 1 | 2 | 3 | 4 | 5 | 6 |
| 5° C. | T04 | −13.89 | 87.46 | 89.36 | 97.56 | 99.41 | 102.29 |
| | T08 | −8.17 | 17.74 | 34.65 | 28.22 | 40.17 | 20.01 |
| | T12 | NP[a] | 35.38 | 40.12 | 48.39 | 53.86 | 45.30 |
| 25° C./ 60% RH | T04 | −35.66 | 58.60 | 88.02 | 59.88 | 88.20 | 65.40 |
| | T08 | −26.35 | 10.10 | 27.28 | 16.17 | 33.54 | 18.20 |
| | T12 | NP[a] | 14.55 | 41.61 | 31.24 | 30.22 | 32.76 |
| 35° C./ 75% RH | T04 | −27.25 | 93.28 | 78.42 | 89.27 | 93.71 | 104.94 |
| | T08 | −39.64 | 3.63 | 33.48 | 5.05 | 23.62 | 1.26 |
| | T12 | NP[a] | 18.58 | 42.65 | 17.48 | 34.17 | 29.55 |
| FZT | T04 | −17.49 | — | — | — | — | — |
| | T08 | — | 17.51 | 35.80 | 21.76 | 39.94 | 22.19 |
| AFT | T04 | −16.59 | 23.34 | 37.23 | 25.37 | 46.39 | 26.76 |

Dynamic Light Scattering

Analyses were performed on sample aliquots diluted to ca. 5 mg/mL in the relevant filtered buffers without polysorbate 80 or sucrose (where those excipients are part of the formulation) using a Malvern APS Zetasizer with 96-well plate auto-sampler. Analyses were performed as indicated on Table 11 with a scattering angle 90° and an upper size range limit of 0.5 μm,

TABLE 11

| Parameter | Size Standard (60 μm) | Protein Sample |
|---|---|---|
| Material | Latex | Protein |
| Solvent | Water | Water |
| Temperature | 25° C. | 25° C. |
| Equilibration time | 120 sec | 120 sec |
| Sampling Speed | Default | Default |
| Cleaning | Vigorous wash[a] | Vigorous wash[a] |
| Measurement Duration | Automatic | Automatic |
| Measurement Number | 3 | 5 |
| Extended duration for large particles | — | Yes |
| Relaxation time multiplier | — | 1000000 |
| Automatic attenuation selection | Yes | Yes |
| Data processing | General Purpose | Protein Analysis |

[a]Rinse Solvent: filtered deionised water; Wash Solvent: 1M NaOH

The parameters considered from the DLS measurements were the % monomer and % Pd (polydispersity) by intensity distribution. The % monomer is not strictly speaking monomer as DLS cannot differentiate between molecules unless they have a size that is at least 6 times bigger than the monomer. The % Pd gives an indication whether the distribution is monodisperse; however, the technique might not be able to detect dimers species. According to the manufacturer literature a distribution with a % Pd less than 23% is monodisperse, less than 28% is nearly monodisperse and more than 28% is polydisperse.

At initial temperature the % monomer by intensity distribution is low (below ca. 80%) for all formulations (data not shown) but formulation 1 (above 90%). Throughout the whole study at 5° C. the values are between ca. 82 and 98% for formulations 2 to 6 except for formulation 3 for which the values observed are ca 66-68. At 25° C., formulations 1, 3 and 4 are the worst performing formulations with % monomer by intensity changing to values below 80% after Tinitial for formulations 1 and 3 and T04 for formulation 4. At 35° C., formulations 1, 3 and 4 are the worst performing formulations with % monomer by intensity changing to values ≤80% after the initial time point. For formulation 5, this change occurs after T04.

With regard to the % Pd, at 5° C. and 25° C. no real trends can be observed across the conditions and formulations with all values being below 23% meaning monodisperse distributions. At 35° C., even though the % Pd is below 23% an increasing trend can be observed across all formulations, Differential Scanning Fluorimetry The method was carried out by Thermofluor using an Applied BioSystem 7500 Fast Real Time PCR Oven. The basis of this method is that when proteins are subjected to increases in temperature they begin to unfold. A dye (the dye is quenched in an aqueous environment but not in a non-polar environment) is added to the protein and as the unfolding takes place the dye binds to exposed hydrophobic regions and emits a fluorescence response which is detected by the detector of the PCR oven. Different regions of the protein have different thermal stabilities hence will unfold at different temperatures. The temperature at which the unfolding occurs is known as the mid-point of thermal denaturation. The higher the temperature, the higher the thermal stability of the protein in a specific environment.

All samples were diluted to 0.12 mg/mL using the relevant formulation buffer. Quadruple replicate preparations were made. As the effect of polysorbate 20, PEG3350 and Benzyl alcohol was not known the following measurements were performed:

Formulation 1 was measured diluted in formulation buffer with and without PEG3350.

Formulations 2 and 4 were measured diluted in formulation buffer with and without PS20.

Formulation 3 was measured diluted in formulation buffer with and without Benzyl alcohol.

Formulations 5 and 6 were measured in their respective formulation buffer.

The dye solution was prepared by mixing 2 μL of 1000× Protein Thermal Shift dye to 250 ul of de-ionised water to obtain an 8× Protein Thermal Shift dye solution.

Sample preparation for the assay is as indicated in Table 12A.

TABLE 12A

| Component | Volume (μL) |
|---|---|
| Protein Thermal Shift Buffer | 5 |
| Sample at 0.12 mg/mL | 12.5 |
| 8X Protein Thermal Shift Dye | 2.5 |

Triplicate samples were prepared in an Applied Biosystems MicroAmp Fast Optical 96-well plate and sealed with an Applied Biosystems MicroAmp Optical adhesive film, Protein Thermal Shift Software was used for data analysis. Only Tm2 could be determined automatically. Tm1 was manually estimated using the first derivative of the thermogram.

In order to be able to differentiate between formulations by DSF the difference in Tm would need to be greater than 2° C. (Table 12B). The results indicated that, at least by DSF, all formulations are similar.

TABLE 12B

| Formulations | Tm1[a] | Tm2[b] |
|---|---|---|
| 1 | 70-72 | 74.5 |
| 2 | 70-72 | 75.0 |
| 3 | 70-72 | 75.2 |
| 4 | 70-72 | 74.7 |
| 5 | 70-72 | 75.2 |
| 6 | 70-72 | 75.2 |

[a]First derivative shoulder;
[b]First derivative main peak

Osmolality

Analyses were performed on an Advanced Micro-Osmometer Model 3320 by freezing point depression using the manufacturer's protocol. Samples were measured in triplicates. Formulations 1 and 6 are below 240 mOsm/kg which is not suitable for sub-cutaneous injection (Table 13).

TABLE 13

| Formulation | Osmolality in mOsm/kg |
|---|---|
| 1 | 168 |
| 2 | 255 |
| 3 | 251 |
| 4 | 408 |
| 5 | 391 |
| 6 | 173 |

Viscosity

Analyses were performed on 76 μL sample aliquots using a TA Instruments DHR-1 Rheometer using a steady state sensing flow sweep method. The geometry used was a 20 mm, 1.99° cone with a solvent trap containing di-ionized water to reduce the evaporation of material during the measurement. For the steady state sensing flow sweep method, the viscosity was averaged for all points at which steady state was reached (acceptance criteria: less or equal to 5% RSD between the points).

Steady State Sensing Flow Sweep
Temperature: 25° C.
Soak Time: 10 sec
Sweep: logarithmic
Shear rate: 2.9 to 287.9 s−1
Points per decade: 5
Steady state sensing: yes
Maximum equilibration time: 180 s
Sample period: 25 s
% tolerance: 5
Consecutive within: 3
Controlled rate: motor mode auto
Data acquisition: 'save point display'
Step termination: none All formulations apart from formulation 6 were considered suitable (Table 14).

TABLE 14

| Formulations | Viscosity at 25° C. in cP (steady state flow sweep) |
|---|---|
| 1 | 13.5 |
| 2 | 13.6 |
| 3 | 12.8 |
| 4 | 14.0 |
| 5 | 12.8 |
| 6 | a | a: failed.

Conclusions

SEC and DLS have been identified as the differentiating assays.

Considering SEC at 5° C., formulation 3 shows an increased rate of aggregation over 12 weeks yet the B22 value is similar to formulations 4 and 5. Also, formulation 2 having a higher B22 value (3.5) than formulations 4, 5 and 6 (2.8-2.9) does not perform better than formulations 4, 5 and 6 while formulation 6 having a negative B22 which would be synonymous with protein-protein net attraction leading to higher aggregation propensity performs similar to 2, 4 and 5. Considering DLS, when stored at 5° C., formulation 6 seemed to behave the best with formulation 3 performing the worst.

It is known that protein self-association is mainly related to colloidal stability, while formation of partially unfolded intermediates is mainly related to conformational stability. However, those 2 aggregation pathways are sometimes difficult to distinguish. Often relative B22 values do not indicate aggregation tendency as similar B22 values could be obtained in different solution conditions irrespective of the different aggregation tendencies or conditions where the measured B22 were more negative that showed less aggregation propensity (Bajaj, H., Sharma, V. K and Kalonia, D. S., 2004, Biophys. J. 87(6), 4048-4054).

In the case of the anti-IL-17A/F Ab exemplified herein, the screening approach using B22 values does not correlate with the aggregation behaviour of this molecule at 160 mg/mL. This could be due to the fact that the mechanisms of aggregation are different at 1 mg/mL and 160 mg/mL or that the tendency of protein self-association is not what primarily governs the degradation/aggregation of this molecule.

In addition, formulations 1 and 6 are below the 240 mOsm/kg threshold, formulations with osmolality below such value are not suitable for sub-cutaneous injection; hence they were not included in further long-term stability evaluation. Formulation 3 was also excluded because of the aggregation rate over 12 weeks.

Example 3: Aggregation Studies

To assess the kinetics of HMW species formation of anti-IL-17A/F antibody according to the invention was studied in 2 formulation buffers:
A: 20 mM Histidine, 250 mM Sorbitol pH6.0 and
B: 55 mM Sodium Acetate, 220 mM Glycine, pH5.0
at 4 different concentrations (80, 120, 160 and 200 mg/mL) of the antibody and of polysorbate 80 (0.02, 0.03, 0.04 and 0.05%, depending on the concentration of the antibody) by SEC over 3 months with numerous time points at 3 storage conditions (5° C., 25° C./60% RH and 35° C./75% RH) of HMW species formation.

The anti-IL-17A/F antibody according to the invention was in an original buffer of 20 mM Histidine; 250 mM Sorbitol pH6.0 at ca 88 mg/mL, so buffer exchange was only performed for buffer B without polysorbate 80 using Vivaflow 50 cassettes with a PES membrane and a WACO of 30 kDa. Three cycles of 2 volumes of formulation buffer B were performed.

The antibody in formulation buffers A and B was concentrated to a nominal target of 120 mg/ml, 160 mg/ml and 200 mg/mL. The concentration values that were not within 5% of the target value were adjusted with the relevant buffer. Concentrations were measured using the SoloVPE (Variable Path Extension system from C. Technologies connected to a Cary50 spectrophotometer) with an extinction coefficient of 1.56 at 280 nm.

All prepared formulations were sterile filtered using Steriflip tubes with a 0.22 μm PVDF membrane except formulation B at 200 mg/mL where PES membrane was used after PVDF membrane was blocked. Sample in formulation A at 200 mg/mL was more easily filtered using PVDF membrane filters while sample in formulation B at 200 mg/mL were more easily filtered using PES membrane filters.

All formulations were spiked with the relevant amount of polysorbate 80 so as to obtain the values listed in Table 15. This was performed in a laminar flow hood.

TABLE 15

| Formulations | PS80 concentration (% w/v) |
|---|---|
| Formulations A and B at 80 mg/mL | 0.02 |
| Formulations A and B at 120 mg/mL | 0.03 |
| Formulations A and B at 160 mg/mL | 0.04 |
| Formulations A and B at 200 mg/mL | 0.05 |

Three 2 mL vials with 1 mL fill volume were prepared for each formulation at each concentration. At each time point the vials were transferred into a laminar flow hood and 2×10 μl aliquots per sample were taken for analysis by SEC followed by sealing of the vial and placement in the relevant storage condition. The reduction in head space by the last time point would not impact the results of the study as the total volume taken from 1 vial was only 260 μL. Storage was performed at 5° C., 25° C./60% RH and 35° C./75% RH at initial time, 1, 2, 3, 4, 5, 7, 10, 14, 18, 28, 42, 56 and 84 days. A further measurement at 168 days was performed for formulation B at 160 mg/ml only.

Size Exclusion Chromatography

Analyses were performed on sample aliquots diluted to 5 mg/mL in filtered mobile phase (0.2 M Na Phosphate pH7.0) using Agilent 1200 series HPLC with 96-well plate autosampler.

Analyses were performed as follows:
Sample load: 50 µL (250 µg) at 5 mg/mL
Column: Tosoh BioScience TSK Gel G3000 SWXL, 250 Å, 5 µm, 7.8×300 mm
Eluent A: 0.2 M Sodium Phosphate, pH7.0
Flow rate: 1 mL/min
Detection: UV (Wavelength: 280 nm, Resolution: 8 nm, reference: off)
Column Temperature: 25° C.
Sample Temperature: 4° C.; Gradient: Isocratic
Max Pressure: 70 bar Run time: 15 min Post time: 5 min
Data analysis was performed using Empower 2 software.

Aggregation rates reported in the Tables 16 and 17 refer to the average monthly rate increase for each formulation, based on the aggregation measured after 3 months or after 6 months, in comparison to the one at T0.

At all concentrations, formulations B were the best performing formulations with a lower aggregation rate over time at 5° C. (Table 16). In addition, after 6 months, the formulation with 55 mM Na acetate, 220 mM Glycine, 0.04% (w/v) PS80 pH 5.0 at a concentration of anti-IL-17A/F Ab of 160 mg/mL showed a similar aggregation rate to the DP formulation or to the rate after 3 months of the formulation at a concentration of anti-IL-17A/F Ab of 80 mg/mL in 20 mM Histidine, 250 mM Sorbitol, 0.02% (w/v) PS80 pH 6.0 at 5° C. (Table 16). There is no significant % LMW species increase over time at 5° C. (data not shown).

TABLE 16

| Formulation | Antibody concentration (mg/ml) | Rate after 3 months | Rate after 6 months |
| --- | --- | --- | --- |
| A | 80 | 0.10 | NP |
| B |  | 0.08 | NP |
| A | 120 | 0.18 | NP |
| B |  | 0.13 | NP |
| A | 160 | 0.25 | NP |

TABLE 16-continued

| Formulation | Antibody concentration (mg/ml) | Rate after 3 months | Rate after 6 months |
| --- | --- | --- | --- |
| B |  | 0.17 | 0.10 |
| A | 200 | 0.33 | NP |
| B |  | 0.21 | NP |
| DP | 80 | 0.13 | 0.10 |
| DS | 80 | 0.23 | 0.17 |

At 25° C., for each concentration, formulations A and B exhibit a comparable aggregation rate over time (Table 17). However, formulation B shows a slightly higher propensity to fragment overtime at 25° C., which results in formulation A being the better performing formulation at 25° C. for all concentrations (data not shown). In particular, at 25° C., the anti-IL17A/F antibody exemplified herein in 55 mM Na acetate, 220 mM Glycine, 0.04% (w/v) PS80 pH5.0 at 160 mg/mL exhibits a slightly higher aggregation rate than when formulated in 20 mM Histidine, 250 mM Sorbitol, 0.02% (w/v) PS80 pH6.0 at 80 mg/mL (Table 17). When compared to the DP and DS (prepared as per example 2), both formulations shown higher aggregation rate at 160 mg/mL and 200 mg/mL whilst at 80 mg/ml and 120 mg/mL formulation B shows a similar aggregation rate than the DP and DS material.

TABLE 17

| Formulation | Antibody concentration (mg/ml) | Rate after 3 months | Rate after 6 months |
| --- | --- | --- | --- |
| A | 80 | 0.34 | NP |
| B |  | 0.37 | NP |
| A | 120 | 0.56 | NP |
| B |  | 0.59 | NP |
| A | 160 | 0.77 | NP |
| B |  | 0.79 | 0.62 |
| A | 200 | 0.97 | NP |
| B |  | 0.97 | NP |
| DP | 80 | 0.43 | 0.30 |
| DS | 80 | 0.57 | 0.37 |

At 35° C., at all concentrations, formulations A performed better overtime with a lower aggregation and fragmentation rate (Table 18 showing the % HMW species), In particular, formulation A at 160 mg/mL exhibits a similar aggregation rate as DP at 80 mg/mL at 40° C. (data not shown). DS and DP were prepared as in Example 2.

TABLE 18

| Formulation | Concentration (mg/ml) | days | | | | | | | | | | | | |
| --- | --- | --- | --- | --- | --- | --- | --- | --- | --- | --- | --- | --- | --- | --- |
|  |  | 0 | 1 | 2 | 3 | 4 | 7 | 10 | 14 | 18 | 28 | 42 | 56 | 84 | 168 |
| A | 80 | 1.37 | 1.44 | 1.47 | 1.55 | 1.58 | 1.68 | 1.78 | 1.97 | 2.08 | 2.16 | 2.68 | 2.88 | 3.43 | NP |
| B |  | 1.17 | 1.27 | 1.32 | 1.40 | 1 41 | 1.53 | 1.69 | 1.88 | 2.11 | 2.21 | 3.13 | 3.60 | 4.75 | NP |
| A | 120 | 1.56 | 1.78 | 1.87 | 2.04 | 2.04 | 2.3 | 2.43 | 2.69 | 2.90 | 3.05 | 3.76 | 4.05 | 4.80 | NP |
| B |  | 1.36 | 1.57 | 1.64 | 1.77 | 1.79 | 2.04 | 2.23 | 2.53 | 2.84 | 2.95 | 4.24 | 4.84 | 6.36 | NP |
| A | 160 | 1.73 | 2.10 | 2.27 | 2.45 | 2.52 | 2.84 | 3.04 | 3.37 | 3.61 | 3.84 | 4.66 | 5.01 | 5.92 | NP |
| B |  | 1.49 | 1.77 | 1.89 | 2.03 | 2.13 | 2.38 | 2.64 | 2.99 | 3.36 | 3.49 | 5.07 | 5.76 | 7.53 | 12.14 |
| A | 200 | 1.97 | 2.49 | 2.68 | 2.95 | 3.04 | 3.43 | 3.65 | 4.07 | 4.40 | 4.69 | 5.67 | 6.12 | 7.24 | NP |
| B |  | 1.70 | 2.10 | 2.25 | 2.43 | 2.53 | 2.88 | 3.2 | 3.66 | 4.12 | 4.25 | 6.47 | 7.37 | 9.59 | NP |

Example 4: Aggregation Study 2

Given the aggregation rate shown by formulation B with 160 mg/ml of anti-IL-17A/F antibody, at both 5° C. and 25° C./60% RH over the DS and DP material (prepared as in example 2), a second aggregation study was performed to validate the results of the first study (example 3) by using non-aged anti-IL-17A/F antibody. Only formulation 55 mM Sodium Acetate, 220 mM Glycine, pH5.0 with 0.02%, 0.03%, 0.04% or 0.05% (w/v) PS80 (PS80 concentration depending on concentration of antibody) at 4 different antibody concentrations (80 mg/ml, 120 mg/ml, 160 mg/ml and 200 mg/mL) at 3 storage conditions (5° C., 25° C./60% RH, 35° C./75% RH) was investigated.

As with aggregation study 1, SEC was used to investigate the sample over 3 months. After 3 months, the formulation at 160 mg/mL was still a good performer that could be considered in a long-term stability evaluation hence this formulation was also tested at 6 months. Buffers' and vials' preparation, storage and SEC methodology was as described for example 3.

Aggregation rates reported in the Tables 19B, 20B and 21B refer to the average monthly rate increase for each formulation, based on the aggregation measured after 3 months or after 6 months, in comparison to the one at T0.

The results of aggregation study 2 confirm the results of aggregation study 1 at 5° C. (Table 19A % HMW species and % LMW species—Table 19B, aggregation rate comparison of studies 1 and 2), at 25° C./60% RH (Table 20A, % HMW species and % LMW species—Table 20B, aggregation rate comparison of studies 1 and 2) and 35° C./75% RH (Table 21A, % HMW species and % LMW species—Table 21B, aggregation rate comparison of studies 1 and 2).

TABLE 19A

| Concentration (mg/ml) | 0 | 7 | 14 | 21 | 28 | 56 | 84 | 168 |
|---|---|---|---|---|---|---|---|---|
| % HMW species | | | | | | | | |
| 80 | 0.76 | 0.77 | 0.79 | 0.80 | 0.85 | 0.87 | 0.94 | 1.02 |
| 120 | 0.90 | NP | 0.96 | 0.96 | 1.02 | 1.10 | 1.18 | 1.31 |
| 160 | 1.00 | 1.03 | 1.08 | 1.12 | 1.21 | 1.28 | 1.41 | 1.58 |
| 200 | 1.09 | 1.14 | 1.22 | 1.25 | 1.32 | 1.48 | 1.60 | 1.78 |
| % LMW species | | | | | | | | |
| 80 | 0.65 | 0.68 | 0.69 | 0.75 | 0.66 | 0.69 | 0.72 | 0.78 |
| 120 | 0.59 | NP | 0.64 | 0.66 | 0.64 | 0.69 | 0.73 | 0.79 |
| 160 | 0.62 | 0.69 | 0.73 | 0.70 | 0.63 | 0.70 | 0.74 | 0.77 |
| 200 | 0.58 | 0.70 | 0.69 | 0.72 | 0.68 | 0.67 | 0.74 | 0.82 |

TABLE 19B

| Aggregation study | Antibody concentration (mg/ml) | Rate after 3 months | Rate after 6 months |
|---|---|---|---|
| 1 | 80 | 0.08 | NP |
| 2 | | 0.06 | 0.04 |
| 1 | 120 | 0.13 | NP |
| 2 | | 0.09 | 0.07 |
| 1 | 160 | 0.17 | 0.10 |
| 2 | | 0.14 | 0.10 |
| 1 | 200 | 0.21 | NP |
| 2 | | 0.17 | 0.12 |
| DP | 80 | 0.13 | 0.10 |
| DS | 80 | 0.23 | 0.17 |

TABLE 20A

| Concentration (mg/ml) | 0 | 7 | 14 | 21 | 28 | 56 | 84 | 168 |
|---|---|---|---|---|---|---|---|---|
| % HMW species | | | | | | | | |
| 80 | 0.76 | 0.88 | 0.99 | 1.05 | 1.16 | 1.41 | 1.69 | 2.30 |
| 120 | 0.90 | 1.12 | 1.29 | 1.38 | 1.51 | 1.92 | 2.28 | 3.10 |
| 160 | 1.00 | 1.34 | 1.61 | 1.77 | 1.96 | 2.51 | 2.96 | 4.05 |
| 200 | 1.09 | 1.54 | 1.85 | 2.00 | 2.20 | 2.82 | 3.32 | 4.53 |
| % LMW species | | | | | | | | |
| 80 | 0.65 | 0.78 | 0.90 | 0.99 | 1.04 | 1.39 | 1.88 | 2.54 |
| 120 | 0.59 | 0.77 | 0.84 | 0.98 | 0.96 | 1.32 | 1.82 | 2.46 |
| 160 | 0.62 | 0.77 | 0.81 | 0.94 | 0.98 | 1.37 | 1.79 | 2.54 |
| 200 | 0.58 | 0.78 | 0.89 | 0.95 | 0.99 | 1.36 | 1.80 | 2.31 |

TABLE 20B

| Aggregation study | Antibody concentration (mg/ml) | Rate after 3 months | Rate after 6 months |
|---|---|---|---|
| 1 | 80 | 0.37 | NP |
| 2 | | 0.31 | 0.26 |
| 1 | 120 | 0.59 | NP |
| 2 | | 0.46 | 0.37 |
| 1 | 160 | 0.79 | 0.62 |
| 2 | | 0.65 | 0.51 |
| 1 | 200 | 0.97 | NP |
| 2 | | 0.74 | 0.57 |
| DP | 80 | 0.43 | 0.30 |
| DS | 80 | 0.57 | 0.37 |

The results shown in Tables 19B, 20B and 21B show that in aggregation study 2 (performed with fresh antibody material) the aggregation rate and fragmentation was slightly lower than in aggregation study 1.

TABLE 21A

| Concentration (mg/ml) | 0 | 7 | 14 | 21 | 28 | 56 | 84 | 168 |
|---|---|---|---|---|---|---|---|---|
| % HMW species | | | | | | | | |
| 80 | 0.76 | 1.14 | 1.45 | 1.66 | 1.91 | 2.85 | 3.85 | 6.60 |
| 120 | 0.90 | 1.45 | 1.93 | 2.21 | 2.54 | 3.80 | 4.95 | 8.15 |
| 160 | 1.00 | 1.85 | 2.45 | 2.83 | 3.23 | 4.71 | 6.11 | 9.91 |
| 200 | 1.09 | 2.10 | 2.77 | 3.17 | 3.64 | 5.24 | 6.74 | 10.81 |
| % LMW species | | | | | | | | |
| 80 | 0.65 | 0.98 | 1.34 | 1.62 | 1.82 | 2.99 | 4.08 | 6.66 |
| 120 | 0.59 | 0.98 | 1.35 | 1.58 | 1.78 | 2.94 | 4.05 | 6.41 |
| 160 | 0.62 | 0.94 | 1.32 | 1.60 | 1.74 | 2.85 | 3.87 | 6.21 |
| 200 | 0.58 | 0.96 | 1.30 | 1.86 | 1.74 | 2.80 | 3.78 | 5.95 |

TABLE 21B

| Aggregation study | Antibody concentration (mg/ml) | Rate after 3 months | Rate after 6 months |
|---|---|---|---|
| 1 | 80 | 1.19 | NP |
| 2 | | 1.03 | 0.97 |
| 1 | 120 | 1.67 | NP |
| 2 | | 1.35 | 1.21 |
| 1 | 160 | 2.01 | 1.78 |
| 2 | | 1.70 | 1.49 |
| 1 | 200 | 2.63 | NP |
| 2 | | 1.88 | 1.62 |

TABLE 21B-continued

| Aggregation study | Antibody concentration (mg/ml) | Rate after 3 months | Rate after 6 months |
|---|---|---|---|
| DP | 80 | 1.27$^a$ | 1.02$^a$ |
| DS | 80 | 1.19 | NP |

$^a$at 40° C./75% RH

Example 5: Long Term Stability Study

Considering the results of both aggregation studies (examples 3 and 4) and the additive screening study at 160 mg/mL (example 2) the following formulations were selected for long term stability evaluation (Table 22). All formulations comprised 160 mg/ml of anti-IL-17A/F Ab exemplified herein and were also subjected to 5 cycles of freeze/thaw.

TABLE 22

| A | 40 mM Sodium Citrate, 50 mM K$_2$HPO$_4$, 75 mM Sucrose, 0.00044% (w/v) PS20, pH 5.6 | Formulation 2 examples 1 and 2 |
|---|---|---|
| B | 40 mM Sodium Citrate, 25 mM K$_2$HPO$_4$, 100 mM Sucrose, 0.00022% (w/v) PS20, pH 5.5 | Formulation 4 examples 1 and 2 |
| C | 40 mM Sodium Acetate, 25 mM K2HPO4, 125 mM Sucrose pH 5.7 | Formulation 5 examples 1 and 2 |
| D | 55 mM Sodium Acetate, 220 mM Glycine, 0.04% (w/v) PS80, pH 5.0 | Formulation B examples 3 and 4 |
| E | 20 mM Histidine, 250 mM Sorbitol, 0.04% PS80, pH 6.0 | Formulation A examples 3 and 4 |

During the formulation preparation buffer exchange cycle for formulations A, B and C took longer than formulation E (~90 minutes for formulations A-C and 50 minutes for formulation E). Formulations A and B behaved similarly and during both the buffer exchange and concentration steps both formulations were cloudy. In addition, the flush for each of these formulations was cloudy and milky in colour. Formulation C was also cloudy during the buffer exchange and concentration steps. There were no noticeable differences for formulations D and E, although E seemed to concentrate and filter the best compared to the other formulations. Osmolality (measured with Precision System Multi-Osmetter 2430), viscosity (measured with Anton Paar Automated Multi Viscometer), pH (Mettler Toledo SevenMulti), visual appearance, absorbance at 280 nm (Agilent 8453 spectrophotometer), SDS-PAGE analysis, cIEF (measured with Protein Simple iCE280 system, see example 2), binding activity (measured with a GE Healthcare Biacore T100 system, subvisible particle analysis by light obscuration (HIAC 9703 system from Hach Lange), CEX-HPLC and SEC-HPLC measurements were performed over a period of 6 months (viscosity and osmolality were only measured at time point 0) at time points 0, 1 month, 2 months, 3 months, 4 months, 6 months. Unless specified, the methods were as described in example 2. After the six-month time point, only formulation D samples were evaluated. For all formulations, a 1.0 mL sample fill volume was used. For the freeze/thaw study, all of the formulations were stored at −70° C. for 12 hours then stored at room temperature until completely thawed (≥2 hours). This was repeated for a total of 5 cycles of freeze/thaw.

Viscosity

Viscosity was measured using an Anton Paar Automated Multi Viscometer. The viscosity values of formulation A to E were tested at time zero. All formulations displayed viscosity values ranging from 2.3-17.3 cP. Samples were evaluated at room temperature (ca.25.00±0.01° C.).

Osmolality

Osmolality has been performed using Precision Systems Multi-Osmetter 2430. No dilution was performed. The osmolality was tested at time zero for all formulations. Osmolality values ranged from 316 mOsm/kg to 450 mOsm/kg.

pH pH has been measured at 25° C. using a Mettler Toledo sevenMulti pH meter. No dilution was performed. The pH was tested for each formulation at each data point. During the first 6 months of stability, the pH of formulations A and B at each time point was 5.5±0.1, the pH of formulation C was 5.7±0.1, and the pH of formulation E was 6.2±0.2. Throughout the 12-month stability, the pH of formulation D was 5.1. No change in pH was observed for any of the five formulations evaluated during the freeze thaw study as compared to time zero.

Appearance

For each time point during the 12 months of stability, including freeze thaw, the appearance for each formulation was evaluated. For all formulations for the first 6 months of stability, the appearance was "yellow brown, clear solution, free of visible particulates". After the 4-month time point, the appearance was determined to be "clear, yellow liquid, free of visible particulates". The change observed in appearance of all formulations can be attributed to analyst variability. As such there were no differences between formulations during the 12 months of stability.

Absorbance at 280 nm

The protein concentrations were determined using an Agilent 8453 spectrophotometer. Samples were diluted gravimetrically to 0.5 mg/mL in their respective buffers. Prior to analysis of each formulation the system was blanked using formulation buffer. No clear trends were observed for the freeze thaw study or over the course of the 12-month stability study suggesting that any changes observed in the concentration were within the variability of the assay. No consistent decrease in concentration was observed for any of the 5 formulations.

SDS-PAGE

SDS-PAGE analysis was performed using a 4-20% Tris-Glycine gel with a 3 μg (non-reducing conditions with IAA) or 4 μg (reducing conditions with DTT) per lane loading. Denaturation was performed by incubating samples at 70° C. for 5 min. Staining used was Colloidal Blue.

Analyses of the stability samples by reduced SDS-PAGE showed no trend (increasing or decreasing) in the % heavy chains (HC)+light chain (LC) for any of the formulations except for the measurements carried out for the accelerated and stressed conditions. A decrease in % HC+LC was observed in all formulations for the 25° C./60% RH condition with a greater decrease observed in the formulations at 40° C./75% RH. For each of the formulations at those conditions, the formation of a new species was observed. No change was observed for any of the formulations evaluated during the freeze thaw study.

Analyses of the stability samples by non-reduced SDS-PAGE showed a general decrease in % IgG observed across all formulations and conditions. The greatest decrease in % IgG was observed for formulations stored at 25° C./60% RH and 40° C./75% RH. The formation of aggregate species was particularly evident in formulation D at 40° C./75% RH. No change was observed for any of the formulations evaluated during the freeze thaw study.

cIEF

The % main peak for formulations stored at −70° C. and 2-8° C. showed little to no change during the 12 months of stability. A decrease was observed in the % main peak area for all formulations stored at 25° C./60% RH with a greater decrease observed when stored at 40° C./75% RH formulations. This decrease was slightly higher in formulation D and slightly lower in formulation E.

For all formulations, there was no change observed in the % acidic species at −70° C. and 2-8° C. An increase in % acidic species for the formulations stored at 25° C./60% RH and 40"C/75% RH formulation was observed. For formulation D, there was a slightly higher increase in % acidic species observed at 25° C./60% RH. At 40° C./75% RH, formulations B and D showed a slightly higher increase in % acidic species while formulation E showed a slightly lower increase.

No significant change in the % basic species was observed for formulations stored at −70° C. and 2-8° C. A slight increase was observed in formulations stored at 25° C./60% RH with an even larger increase in % basic species observed in formulation A with storage at 40° C./75% RH. At the 2-month time point, there was a loss of resolution due to capillary issues causing a decrease in % basic species for all formulations and conditions. For all time points, there was greater variability in % basic species.

No changes in acidic, main or basic species were observed in freeze thaw formulations A to E.

Biacore

Binding of IL-17A and IL-17F was measured using a Biacore T100 (GE Healthcare). All experiments were performed at 25° C. Affinipure F(ab')2 fragment goat anti-human IgG, Fc fragment specific (Jackson ImmunoResearch, category #109-006-098, lot #83295) was immobilized on a CM5 Sensor Chip (Biacore AB, category #BR1000-14, different chips used from lot #10030608) via amine coupling chemistry to a capture level of ca. 7000 response units (RUs). HBS-EP buffer (10 mM HEPES pH 7.4, 0.15 M NaCl, 3 mM EDTA, 0.005% Surfactant P20, GE Healthcare) was used as the running buffer with a flow rate of 10 μL/min. A 10 μL injection of each sample of antibody at 0.5 μg/mL was used for capture. Recombinant Human IL-17A (R&D Systems, catalog number 317-ILB) and IL-17F (R&D Systems, catalog number 1335-IL) were titrated over the captured anti-IL17AF antibody at doubling dilutions from 10 nM to 2.5 nM and from 10 nM to 1.25 nM respectively at a flow rate of 30 μL/min. The surface was regenerated at a flow rate of 10 uL/min by a 10 μL injection of 40 mM HCl, followed by a 5 μL injection of 5 mM NaOH.

Double referenced background subtracted binding curves were analyzed using the BIAevaluation software (version 3.2) following standard procedures. Kinetic parameters were determined from the fitting algorithm (Biacore 1:1 Langmuir binding fit).

No trends were observed in the binding activity over the first 12 months of stability suggesting that changes in $K_D$ were within the variation of the assay. An evaluation of freeze thaw study samples was performed in parallel with the 1-month stability samples. There were no changes observed for these samples and slight changes in $K_D$ are within the variation of the assay.

Size Exclusion Chromatography

SEC was performed on sample aliquots diluted to 1 mg/mL in filtered eluent A using an Agilent 1200 series system with the following parameters:

Sample load: 20 μL (20 μg) at 1 mg/mL
Column: Tosoh BioScience TSK Gel G3000 SWXL, 250 Å, 5 μm, 7.8×300 mm (part number: 8541)
Eluent A: 0.05 M $Na_2HPO_4$, 0.25 M NaCl pH7.2
Flow rate: 05 mL/min
Detection: UV (Wavelength: 280 nm, Resolution: 8 nm, reference: off)
Column Temperature: 20±5° C.
Sample Temperature: 6±2° C.
Gradient: Isocratic
Max Pressure: 70 bar
Run time: 35 min For all formulations, there was no change observed in the % main peak at −70° C. and a slight change observed at 2-8° C. A decrease in the % main peak was observed for all formulations stored at 25° C./60% RH and an even greater decrease for formulations stored at 40° C./75% RH. Overall, formulation D showed the greatest decrease in % main peak over the 6 months of stability at 25° C./60% RH and 3 months stability at 40° C./75% RH.

No significant change was observed in the % HMW and % LMW species in all formulations stored at −70° C. There was a slight increase in % HMW but no noticeable change in % LMW for formulations stored at 2-8° C. Over the six months of stability, the rate of aggregation was lower for formulations A, B and D compared to formulation C and E. For the 25° C./60% RH and 40° C./75% RH conditions an increase was observed for both the HMW and LMW species. Formulation D showed the greatest increase for both the HMW and LMW species over the 6 months stability at 25° C./60% RH and over the 3 months stability at 40° C./75% RH.

No changes were observed for any of the formulations evaluated during freeze thaw study.

Cation Exchange Chromatography

CEX was performed on sample aliquots diluted to 1 mg/mL in eluent A using an Agilent 1100 system with the following parameters:

Sample load: 20 μL (20 μg)
Column: BioMAb, NPS, PK, 4.6*250 mm #Agilent 5190-2407
Eluent A: 10 mM Sodium phosphate pH6.0
Eluent B: 10 mM Sodium phosphate, 1 M NaCl, pH6.0
Flow rate: 1 mL/min
Wavelength: 220 nm bandwidth 8 nm/220 nm bandwidth 8 nm, reference 360 nm bandwidth 100, slit 4 nm
Peak width: 0.1 min (2 s)
Column temperature: 25° C.
Sample temperature: 4° C.
Gradient:

| Time (min) | % B |
|---|---|
| 0 | 2 |
| 40 | 15 |
| 40.02 | 100 |
| 45 | 100 |
| 45.02 | 2 |
| 60 | 2 |

For all formulations and conditions during the 12 months stability, there was no change in % main peak area for the −70° C. or 2-8° C. conditions. A decrease was observed at 25° C./60% RH and even greater decrease at the stressed condition 40° C./75% RH. At 25° C./60% RH, all formulations behaved similarly within the variability of the assay. At 40° C./75% RH, formulations A, B, C and D behaved similarly with formulation E showing less of a decrease. The % area for the acidic and basic species did not change over the 12-month study for formulations stored at −70° C. and 2-8° C. However, the decrease in % main peak for formulations stored at 25° C./60% RH and 40° C./75% RH corresponds mainly to an increase in the % area of the acidic species with a smaller increase observed in the % area of the basic species. All formulations behaved similarly within the variability of the assay. The CEX method has a high variability—5% for acidic species and 9% for the basic species.

No changes were observed for the freeze thaw stress samples in the % main, % acidic or % basic peak areas.

HIAC

Sub-visible particle analysis by light obscuration was performed using a HACH Lange HIAC9703 system by diluting 200 μL of sample into 1000 μL of WFI. Two 500 μL draws were analysed for particles ≥2, 5, 10 and 25 μm particles and the data from the second draw was corrected for dilution (results multiplied by 5) and reported as particles/mL.

The results were fairly consistent over the course of 12 months with differences occurring due to the variability within the assay. No changes were observed for the freeze thaw stress samples.

Conclusions

When samples are stored at 2-8'C condition, only the SEC results showed any differentiation between the formulations. All formulations show similar low levels of fragmentation, however, formulations A, B and D show the lowest aggregation over the course of the study with D exhibiting a lower initial level of HMW species. The SEC results combined with the processing observations leads to the conclusion that, given that the formulation's shelf-life is intended to be at 5° C. and not under conditions similar to those used in the accelerated or stress studies, formulation D was the best performer at 2-8° C. followed by formulation E, also in light of the fact that formulation D at 160 mg/ml of anti-IL-17A/F Ab had a comparable profile to the DP at 80 mg/ml and reduced processing issues.

Example 6: 3-Months Formulation Robustness Screen Study of Selected Formulations A DoE using a fractional factorial design with 3 centre points was generated with the JMP version 11 statistical software from SAS. It was intended for a primary screening of the following formulation variables by testing the main effects and interactions over 12 weeks at 2 conditions 5±3° C. and 25±2° C./60±5% RH:

acetate concentration (55 mM±20%)

glycine concentration (220 mM±20%)

Polysorbate 80 concentration (0.04%±0.02%)

pH (4.9±0.3)

Protein concentration (160±15%)

The formulations comprising the anti-IL17A/F antibody exemplified herein were made as detailed in Table 23. Formulation 20 was added to evaluate the impact on stability of low protein and excipients concentrations. The formulations were prepared by buffer exchanging the anti-IL17A/F antibody exemplified herein at 50 mg/mL in the relevant formulation detailed in Table 23 without PS80. Seven cycles were performed before the protein concentration was adjusted to the target concentration listed in Table 23. Formulation 20 was prepared by dilution of formulation 9. A 10% stock solution of PS80 was used to spike each formulation to reach the target PS80 concentration detailed in Table 23.

TABLE 23

| Formulations | target protein conc | measured conc | Acetate (mM) | Glycine (mM) | Polysorbate 80 (w/v) | osmolality | DF buffer pH | Measured pH at 24.0° C. | pH shift |
|---|---|---|---|---|---|---|---|---|---|
| F1 | 160 | 160.0 | 55 | 220 | 0.04 | 350 | 4.90 | 5.02 | 0.12 |
| F2 | 136 | 138.2 | 66 | 264 | 0.02 | 405 | 5.21 | 5.28 | 0.07 |
| F3 | 136 | 135.8 | 66 | 176 | 0.02 | 291 | 4.60 | 4.75 | 0.15 |
| F4 | 136 | 134.8 | 44 | 176 | 0.06 | 262 | 4.60 | 4.80 | 0.21 |
| F5 | 184 | 186.4 | 44 | 176 | 0.06 | 310 | 5.20 | 5.35 | 0.15 |
| F6 | 184 | 188.1 | 66 | 264 | 0.02 | 432 | 4.60 | 4.81 | 0.21 |
| F7 | 136 | 135.1 | 44 | 264 | 0.06 | 363 | 5.21 | 5.31 | 0.10 |
| F8 | 136 | 134.8 | 66 | 264 | 0.06 | 377 | 4.61 | 4.76 | 0.15 |
| F9 | 136 | 134.4 | 44 | 176 | 0.02 | 277 | 5.20 | 5.31 | 0.10 |
| F10 | 184 | 190.3 | 44 | 264 | 0.06 | 398 | 4.60 | 4.90 | 0.30 |
| F11 | 136 | 137.0 | 44 | 264 | 0.02 | 354 | 4.61 | 4.84 | 0.23 |
| F12 | 184 | 184.5 | 44 | 176 | 0.02 | 293 | 4.60 | 4.88 | 0.28 |
| F13 | 184 | 185.8 | 44 | 264 | 0.02 | 402 | 5.20 | 5.35 | 0.15 |
| F14 | 184 | 187.1 | 66 | 264 | 0.06 | 442 | 5.21 | 5.30 | 0.08 |
| F15 | 160 | 161.9 | 55 | 220 | 0.04 | 349 | 4.90 | 5.05 | 0.15 |
| F16 | 160 | 160.3 | 55 | 220 | 0.04 | 344 | 4.90 | 5.04 | 0.14 |
| F17 | 136 | 137.2 | 66 | 176 | 0.06 | 311 | 5.18 | 5.25 | 0.07 |
| F18 | 184 | 184.5 | 66 | 176 | 0.06 | 326 | 4.60 | 4.81 | 0.21 |
| F19 | 184 | 184.3 | 66 | 176 | 0.02 | 355 | 5.20 | 5.31 | 0.11 |
| F20 | 68 | 69.9 | 44 | 176 | 0.02 | 262 | 5.20 | 5.26 | 0.06 |

After sterile filtration, 1 mL of each formulation was transferred into 2 mL Schott Type 1 Glass vials sealed with Flurotec coated Westar stoppers and Tru-Edge Flip off seals for initial testing and storage at 5±3° C. and 25±2° C./60±5% RH.

pH and osmolality detailed in Table 23 were measured at Tinitial while visual assessment as well as SEC and iCE were performed at 4, 8 and 12 weeks (T12w). SEC was performed on sample aliquots diluted to 1 mg/mL in filtered eluent A (0.05 M $Na_2HPO_4$, 0.25 M NaCl pH7.2) using an Agilent 1200 series system with the following parameters:

Sample load: 20 µL (20 µg) at 1 mg/mL

Column: Tosoh BioScience TSK Gel G3000 SWXL 250 Å, 5 µm, 7.8×300 mm (part number: 8541)

Flow rate: 0.5 mL/min

Detection: UV (Wavelength: 280 nm, Resolution: 8 nm, reference: off)

Column Temperature: 20±5° C.

Sample Temperature: 6±2° C.

Gradient: Isocratic

Max Pressure: 70 bar

Run time: 35 min

Data analysis was performed using Empower 3 software.

For all formulations, no significant changes were observed in the % LMW species in all formulations stored at 5° C., but with an increase observed for all formulations when stored at 25° C. As expected, some increase in % HMW species over 12 weeks across all the formulations was observed, with formulations stored at 25° C. showing a more pronounced increase than those stored at 5° C. (Table 24).

Imaged Capillary Electrophoresis was performed using a Protein Simple iCE3 system.

Analyses were Performed as Follows:

Samples were diluted to a nominal concentration of 20 mg/mL then to a concentration of 2 mg/mL with filtered de-ionized water. Analyses were performed on samples at 0.2 mg/mL (1/10 dilution in master mix of the samples at 2 mg/mL). A master mix with the following components was prepared (Table 25).

TABLE 25

| 1% MC | Pharmalytes 3-10 | pI marker 4.65 | pI marker 9.50 | 4M Urea |
|---|---|---|---|---|
| 70 µL | 8 µL | 1 µL | 1 µL | 100 µL |

The focus parameters were as follows: 1 min at 1500 Volts followed by 6 min at 3000 Volts. As shown in Table 26, for all formulations, no significant changes were observed in % acidic and % basic species for formulations stored at 5° C. As for the % HMW species, formulations stored at 25° C. showed a more pronounced increase in % acidic and basic species than those stored at 5° C. (Table 26).

TABLE 24

| Formulations | T12w SEC % HMW | Delta over 3M | T12w SEC % Mono | Delta over 3M | T12w SEC % LMW | Delta over 3M |
|---|---|---|---|---|---|---|
| 5° C. | | | | | | |
| F1 | 2.39 | 0.65 | 96.53 | −0.76 | 1.08 | 0.11 |
| F2 | 2.38 | 0.65 | 96.57 | −0.75 | 1.05 | 0.10 |
| F3 | 2.06 | 0.55 | 96.86 | −0.66 | 1.08 | 0.12 |
| F4 | 2.02 | 0.50 | 96.90 | −0.61 | 1.09 | 0.11 |
| F5 | 2.88 | 0.81 | 96.06 | −0.91 | 1.06 | 0.09 |
| F6 | 2.41 | 0.71 | 96.50 | −0.83 | 1.09 | 0.12 |
| F7 | 2.38 | 0.65 | 96.54 | −0.79 | 1.08 | 0.14 |
| F8 | 1.99 | 0.49 | 96.93 | −0.58 | 1.08 | 0.09 |
| F9 | 2.42 | 0.66 | 96.52 | −0.76 | 1.06 | 0.10 |
| F10 | 2.50 | 0.73 | 96.43 | −0.82 | 1.06 | 0.09 |
| F11 | 1.99 | 0.50 | 96.92 | −0.61 | 1.08 | 0.10 |
| F12 | 2.47 | 0.72 | 96.46 | −0.82 | 1.07 | 0.09 |
| F13 | 2.78 | 0.86 | 96.18 | −0.93 | 1.05 | 0.08 |
| F14 | 2.87 | 0.86 | 96.07 | −0.94 | 1.06 | 0.08 |
| F15 | 2.30 | 0.60 | 96.64 | −0.69 | 1.06 | 0.09 |
| F16 | 2.37 | 0.65 | 96.57 | −0.74 | 1.05 | 0.08 |
| F17 | 2.41 | 0.65 | 96.53 | −0.74 | 1.06 | 0.09 |
| F18 | 2.44 | 0.69 | 96.47 | −0.79 | 1.09 | 0.10 |
| F19 | 2.93 | 0.90 | 96.01 | −0.99 | 1.06 | 0.09 |
| F20 | 1.85 | 0.39 | 97.07 | −0.51 | 1.08 | 0.12 |
| 25° C. | | | | | | |
| F1 | 4.21 | 2.47 | 93.56 | −3.73 | 2.23 | 1.26 |
| F2 | 4.43 | 2.70 | 93.60 | −3.72 | 1.97 | 1.02 |
| F3 | 3.45 | 1.94 | 93.89 | −3.63 | 2.66 | 1.70 |
| F4 | 3.38 | 1.86 | 94.13 | −3.38 | 2.49 | 1.51 |
| F5 | 5.11 | 3.04 | 93.00 | −3.97 | 1.88 | 0.91 |
| F6 | 4.56 | 2.86 | 92.81 | −4.52 | 2.63 | 1.66 |
| F7 | 4.30 | 2.57 | 93.73 | −3.60 | 1.97 | 1.03 |
| F8 | 3.54 | 2.04 | 93.80 | −3.71 | 2.66 | 1.67 |
| F9 | 4.15 | 2.39 | 93.90 | −3.38 | 1.95 | 0.99 |
| F10 | 4.68 | 2.91 | 92.91 | −4.34 | 2.41 | 1.44 |
| F11 | 3.50 | 2.01 | 94.01 | −3.52 | 2.48 | 1.50 |
| F12 | 4.44 | 2.69 | 93.21 | −4.07 | 2.35 | 1.37 |
| F13 | 5.43 | 3.51 | 92.67 | −4.44 | 1.91 | 0.94 |
| F14 | 5.43 | 3.42 | 92.65 | −4.36 | 1.92 | 0.94 |
| F15 | 4.23 | 2.53 | 93.59 | −3.74 | 2.18 | 1.21 |
| F16 | 4.39 | 2.67 | 93.44 | −3.87 | 2.17 | 1.20 |
| F17 | 4.12 | 2.36 | 93.90 | −3.37 | 1.99 | 1.02 |
| F18 | 4.43 | 2.68 | 93.02 | −4.24 | 2.55 | 1.56 |
| F19 | 5.30 | 3.27 | 92.78 | −4.22 | 1.92 | 0.95 |
| F20 | 4.21 | 2.47 | 93.56 | −3.73 | 2.23 | 1.26 |

TABLE 26

| Formulations | iCE % acidic | Delta over 3M | iCE % Main | Delta over 3M | iCE % basic | Delta over 3M |
|---|---|---|---|---|---|---|
| 5° C. | | | | | | |
| F1 | 50.3 | 0.8 | 45.4 | −1.0 | 4.2 | 0.2 |
| F2 | 50.4 | 0.8 | 45.6 | −0.3 | 4.0 | −0.5 |
| F3 | 49.8 | 0.4 | 46.1 | −0.2 | 4.1 | −0.2 |
| F4 | 49.9 | −0.2 | 45.8 | 0.7 | 4.2 | −0.5 |
| F5 | 50.5 | 0.2 | 45.5 | −0.6 | 4.1 | 0.4 |
| F6 | 50.2 | 0.3 | 45.7 | −0.2 | 4.1 | −0.1 |
| F7 | 50.3 | 0.1 | 45.7 | 0.1 | 4.1 | −0.3 |
| F8 | 49.6 | −0.4 | 45.9 | 0.5 | 4.4 | −0.1 |
| F9 | 50.2 | 0.9 | 46.0 | −0.5 | 3.9 | −0.4 |
| F10 | 50.5 | 0.4 | 45.1 | −0.7 | 4.4 | 0.3 |
| F11 | 50.4 | 0.5 | 45.5 | −0.6 | 4.2 | 0.1 |
| F12 | 50.4 | 1.4 | 45.3 | −1.4 | 4.3 | 0.0 |
| F13 | 50.2 | 1.3 | 45.6 | −1.1 | 4.2 | −0.2 |
| F14 | 50.5 | 0.6 | 45.3 | −0.5 | 4.2 | −0.1 |
| F15 | 50.0 | 0.3 | 45.6 | −0.5 | 4.4 | 0.2 |
| F16 | 50.3 | 1.2 | 45.7 | −1.0 | 4.1 | −0.2 |
| F17 | 50.0 | 1.2 | 46.1 | −0.9 | 4.0 | −0.3 |
| F18 | 49.8 | −0.3 | 46.0 | 0.2 | 4.2 | 0.2 |
| F19 | 50.5 | 0.6 | 45.4 | −0.3 | 4.2 | −0.3 |
| F20 | 49.9 | −0.8 | 45.9 | 0.8 | 4.2 | 0.0 |
| 25° C. | | | | | | |
| F1 | 55.34 | 5.79 | 39.4 | −7.0 | 5.3 | 1.2 |
| F2 | 55.99 | 6.39 | 39.3 | −6.6 | 4.7 | 0.2 |
| F3 | 54.13 | 4.75 | 39.9 | −6.3 | 5.9 | 1.6 |
| F4 | 54.99 | 4.88 | 39.3 | −5.8 | 5.7 | 1.0 |
| F5 | 55.75 | 5.50 | 39.7 | −6.4 | 4.6 | 0.9 |
| F6 | 54.90 | 5.01 | 39.2 | −6.8 | 5.9 | 1.8 |
| F7 | 56.50 | 6.39 | 38.6 | −6.9 | 4.9 | 0.5 |
| F8 | 55.21 | 5.13 | 38.9 | −6.5 | 5.9 | 1.4 |
| F9 | 55.53 | 6.23 | 39.6 | −6.9 | 4.9 | 0.6 |
| F10 | 55.34 | 5.24 | 39.1 | −6.7 | 5.6 | 1.5 |
| F11 | 55.33 | 5.52 | 38.9 | −7.2 | 5.8 | 1.7 |
| F12 | 54.66 | 5.73 | 39.3 | −7.4 | 6.0 | 1.7 |
| F13 | 56.05 | 7.14 | 39.5 | −7.3 | 4.5 | 0.1 |
| F14 | 56.08 | 6.17 | 39.2 | −6.6 | 4.7 | 0.4 |
| F15 | 55.11 | 5.37 | 39.6 | −6.5 | 5.3 | 1.1 |
| F16 | 54.66 | 5.54 | 40.0 | −6.7 | 5.3 | 1.1 |
| F17 | 55.30 | 6.50 | 39.8 | −7.2 | 5.0 | 0.7 |
| F18 | 54.20 | 4.10 | 39.6 | −6.2 | 6.2 | 2.1 |
| F19 | 55.09 | 5.20 | 39.6 | −6.1 | 5.3 | 0.9 |
| F20 | 54.89 | 4.27 | 40.2 | −4.9 | 4.9 | 0.6 |

The invention claimed is:

1. A pharmaceutical composition comprising:
   a. from about 120 mg/ml to about 180 mg/ml of an antibody, or an antigen-binding fragment thereof, comprising a heavy chain variable region comprising SEQ ID NO:1 and a light chain variable region comprising SEQ ID NO:2;
   b. about 40 mM to about 90 mM acetate;
   c. about 160 mM to about 300 mM of glycine;
   d. about 0.02% to about 0.06% (w/v) polysorbate 80 and; having pH of from about 4.6 to about 5.5.

2. The pharmaceutical composition according to claim 1, wherein the composition comprises from about 176 mM to about 264 mM of glycine.

3. The pharmaceutical composition according to claim 1, wherein the composition comprises from about 44 mM to about 66 mM acetate.

4. The pharmaceutical composition according to claim 1, wherein the antibody or antigen-binding fragment thereof specifically binds human IL-17A and human IL17F.

5. The pharmaceutical composition according to claim 1, wherein the composition comprises:
   a. from about 120 mg/mL to about 180 mg/mL of antibody, or antigen-binding fragment thereof;
   b. from about 44 mM to about 66 mM acetate;
   c. from about 176 mM to about 264 mM glycine;
   d. from about 0.02% to about 0.06% (w/v) polysorbate 80, wherein the composition has a pH of from about 4.6 to about 5.5.

6. A method for preparing a pharmaceutical composition, wherein the method comprises:
   a) preparing a low concentration of formulation by combining from about 40 mg/ml to about 50 mg/ml of an antibody, or an antigen-binding fragment thereof, comprising a heavy chain variable region comprising the SEQ ID NO:1 and a light chain variable region comprising the SEQ ID NO:2 with a buffer comprising glycine and acetate at pH of from about 4.6 to about 5.5;

b) preparing a high concentration formulation by concentrating the antibody or antigen-binding fragment thereof the low concentration formulation obtained in a) to a concentration of about 160 mg/ml to about 180 mg/ml;

c) adding to the high concentration formulation obtained in b) about 0.02% to about 0.06% polysorbate 80; and d) before step c) adjusting the concentration of the antibody or antigen-binding fragment thereof so the buffer comprising about 40 to about 90 mM of acetate and about 160 mM to about 300 mM of glycine.

7. A pharmaceutical composition obtained by claim 6.

8. The pharmaceutical composition according to claim 7, wherein the pH of the composition is from about 4.6 to about 5.5.

9. The pharmaceutical composition according to claim 1, comprising 160 mg/ml of the antibody, or antigen-binding fragment thereof.

\* \* \* \* \*

SEQUENCE LISTING

<160> NUMBER OF SEQ ID NOS: 4

<210> SEQ ID NO 1
<211> LENGTH: 125
<212> TYPE: PRT
<213> ORGANISM: Artificial sequence
<220> FEATURE:
<223> OTHER INFORMATION: Heavy chain variable region

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser
        115                 120                 125

<210> SEQ ID NO 2
<211> LENGTH: 107
<212> TYPE: PRT
<213> ORGANISM: Artificial sequence
<220> FEATURE:
<223> OTHER INFORMATION: Light chain variable region

<400> SEQUENCE: 2

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
        35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys
            100                 105

<210> SEQ ID NO 3
<211> LENGTH: 455
<212> TYPE: PRT
<213> ORGANISM: Artificial sequence
<220> FEATURE:
<223> OTHER INFORMATION: Heavy Chain

<400> SEQUENCE: 3

Glu Val Gln Leu Val Glu Ser Gly Gly Gly Leu Val Gln Pro Gly Gly
1               5                   10                  15

-continued

Ser Leu Arg Leu Ser Cys Ala Ala Ser Gly Phe Thr Phe Ser Asp Tyr
         20                  25                  30

Asn Met Ala Trp Val Arg Gln Ala Pro Gly Lys Gly Leu Glu Trp Val
         35                  40                  45

Ala Thr Ile Thr Tyr Glu Gly Arg Asn Thr Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Ser Pro Pro Gln Tyr Tyr Glu Gly Ser Ile Tyr Arg Leu Trp Phe
             100                 105                 110

Ala His Trp Gly Gln Gly Thr Leu Val Thr Val Ser Ser Ala Ser Thr
             115                 120                 125

Lys Gly Pro Ser Val Phe Pro Leu Ala Pro Ser Ser Lys Ser Thr Ser
 130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                 165                 170                 175

Thr Phe Pro Ala Val Leu Gln Ser Ser Gly Leu Tyr Ser Leu Ser Ser
             180                 185                 190

Val Val Thr Val Pro Ser Ser Ser Leu Gly Thr Gln Thr Tyr Ile Cys
         195                 200                 205

Asn Val Asn His Lys Pro Ser Asn Thr Lys Val Asp Lys Lys Val Glu
         210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                 245                 250                 255

Asp Thr Leu Met Ile Ser Arg Thr Pro Glu Val Thr Cys Val Val Val
             260                 265                 270

Asp Val Ser His Glu Asp Pro Glu Val Lys Phe Asn Trp Tyr Val Asp
         275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                 325                 330                 335

Pro Ala Pro Ile Glu Lys Thr Ile Ser Lys Ala Lys Gly Gln Pro Arg
             340                 345                 350

Glu Pro Gln Val Tyr Thr Leu Pro Pro Ser Arg Asp Glu Leu Thr Lys
         355                 360                 365

Asn Gln Val Ser Leu Thr Cys Leu Val Lys Gly Phe Tyr Pro Ser Asp
     370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                 405                 410                 415

Lys Leu Thr Val Asp Lys Ser Arg Trp Gln Gln Gly Asn Val Phe Ser
             420                 425                 430

```
<210> SEQ ID NO 4
<211> LENGTH: 214
<212> TYPE: PRT
<213> ORGANISM: Artificial sequence
<220> FEATURE:
<223> OTHER INFORMATION: Light chain

<400> SEQUENCE: 4

Ala Ile Gln Leu Thr Gln Ser Pro Ser Ser Leu Ser Ala Ser Val Gly
 1               5                  10                  15

Asp Arg Val Thr Ile Thr Cys Arg Ala Asp Glu Ser Val Arg Thr Leu
                20                  25                  30

Met His Trp Tyr Gln Gln Lys Pro Gly Lys Ala Pro Lys Leu Leu Ile
            35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```